(12) United States Patent
Flom et al.

(10) Patent No.: US 10,925,621 B2
(45) Date of Patent: Feb. 23, 2021

(54) FLEXIBLE DRILL BIT AND ANGLED DRILL GUIDE FOR USE WITH THE SAME

(71) Applicant: Stryker Puerto Rico Limited, Arroyo, PR (US)

(72) Inventors: James Flom, Redwood City, CA (US); J. Brook Burley, Mountain View, CA (US); Jeremy Graul, Elk Grove, CA (US); Sudip Pandya, Fremont, CA (US)

(73) Assignee: Stryker Puerto Rico Limited, Arroyo, PR (US)

( * ) Notice: Subject to any disclaimer, the term of this patent is extended or adjusted under 35 U.S.C. 154(b) by 0 days.

(21) Appl. No.: 15/854,347

(22) Filed: Dec. 26, 2017

(65) Prior Publication Data
US 2018/0185037 A1 Jul. 5, 2018

Related U.S. Application Data

(63) Continuation of application No. 13/764,565, filed on Feb. 11, 2013, now Pat. No. 9,848,894, which is a continuation-in-part of application No. 13/735,806, filed on Jan. 7, 2013, now Pat. No. 10,582,935.

(60) Provisional application No. 61/583,265, filed on Jan. 5, 2012, provisional application No. 61/596,993, filed on Feb. 9, 2012.

(51) Int. Cl.
*A61B 17/16* (2006.01)
*A61B 17/17* (2006.01)
*A61B 90/00* (2016.01)

(52) U.S. Cl.
CPC .......... *A61B 17/17* (2013.01); *A61B 17/1615* (2013.01); *A61B 17/1631* (2013.01); *A61B 17/1633* (2013.01); *A61B 17/1746* (2013.01); *A61B 2090/062* (2016.02)

(58) Field of Classification Search
CPC ............ A61B 17/1615; A61B 17/1631; A61B 17/1633; A61B 17/17
USPC ....................................... 606/79–85
See application file for complete search history.

(56) References Cited

U.S. PATENT DOCUMENTS

| | | |
|---|---|---|
| 4,541,423 A | 9/1985 | Barber |
| 5,387,218 A | 2/1995 | Meswania |
| 5,601,550 A | 2/1997 | Esser |
| 5,733,290 A | 3/1998 | McCue et al. |
| 6,309,396 B1 | 10/2001 | Ritland |
| 6,422,010 B1 | 7/2002 | Julien |
| 6,423,080 B1 | 7/2002 | Gellman et al. |
| 2005/0054953 A1 | 3/2005 | Ryan et al. |
| 2005/0059975 A1 | 3/2005 | Fanger et al. |
| 2005/0203527 A1 | 9/2005 | Carrison et al. |

(Continued)

FOREIGN PATENT DOCUMENTS

| | | |
|---|---|---|
| EP | 1584299 | 10/2005 |
| WO | WO 2011/161676 | 12/2011 |
| WO | WO 2014/107729 | 7/2014 |

*Primary Examiner* — Si Ming Ku
(74) *Attorney, Agent, or Firm* — Pandiscio & Pandiscio

(57) ABSTRACT

Apparatus for drilling a hole in material, the apparatus comprising:
an angled drill guide comprising a curved distal section, a less-curved proximal section, and a lumen extending therebetween, wherein the less-curved proximal section comprises a flat extending therealong for reducing the effective diameter of the less-curved proximal section so as to minimize interference between the angled drill guide and the side wall of an access cannula.

27 Claims, 40 Drawing Sheets

(56) References Cited

U.S. PATENT DOCUMENTS

| | | | |
|---|---|---|---|
| 2007/0264093 A1 | 11/2007 | White et al. | |
| 2008/0188854 A1* | 8/2008 | Moser | A61B 17/0401 606/80 |
| 2008/0221620 A1* | 9/2008 | Krause | A61B 17/7028 606/255 |
| 2009/0012526 A1* | 1/2009 | Fletcher | A61B 17/1615 606/96 |
| 2009/0149890 A1 | 6/2009 | Martin | |
| 2009/0204121 A1 | 8/2009 | Cavallazzi et al. | |
| 2010/0191248 A1 | 7/2010 | Mehta et al. | |
| 2010/0286694 A1 | 11/2010 | Rio et al. | |
| 2010/0292722 A1 | 11/2010 | Klaue | |
| 2011/0015674 A1 | 1/2011 | Howard et al. | |
| 2011/0071545 A1 | 3/2011 | Pamichev et al. | |
| 2011/0144703 A1* | 6/2011 | Krause | A61B 17/8625 606/309 |
| 2011/0208194 A1 | 8/2011 | Steiner et al. | |
| 2011/0251621 A1 | 10/2011 | Sluss et al. | |
| 2012/0089188 A1* | 4/2012 | Jackson | A61B 17/702 606/254 |
| 2012/0123417 A1 | 5/2012 | Smith | |
| 2012/0203231 A1* | 8/2012 | Long | A61B 17/1631 606/80 |
| 2013/0158596 A1 | 6/2013 | Miller et al. | |
| 2014/0107657 A1 | 4/2014 | Norton et al. | |

* cited by examiner

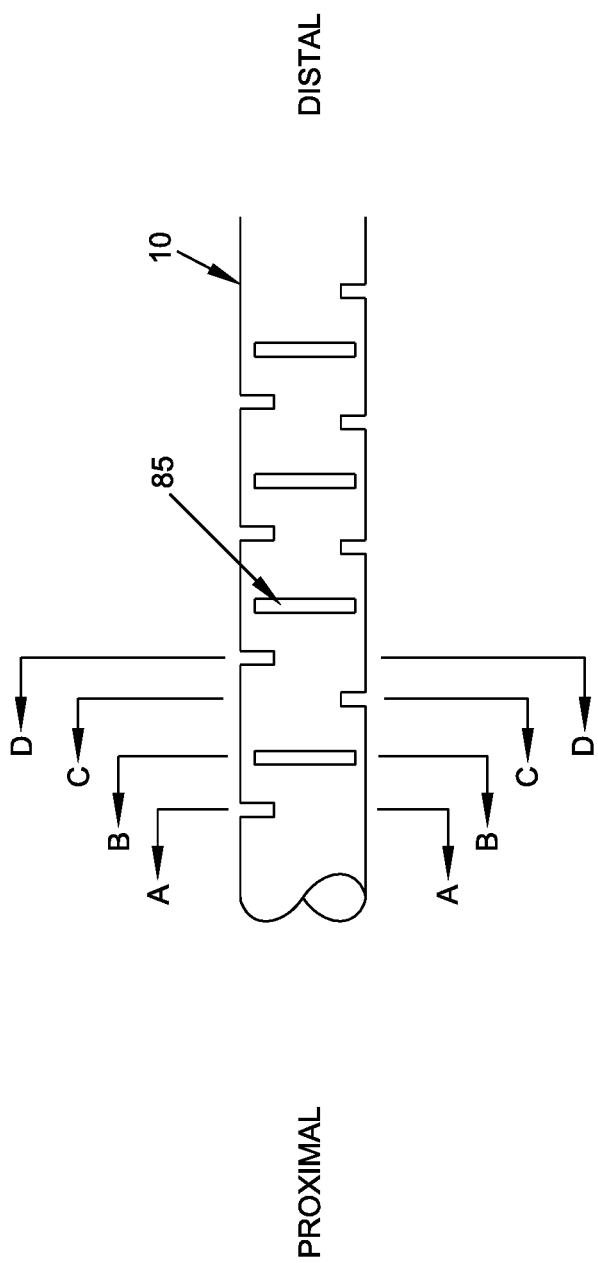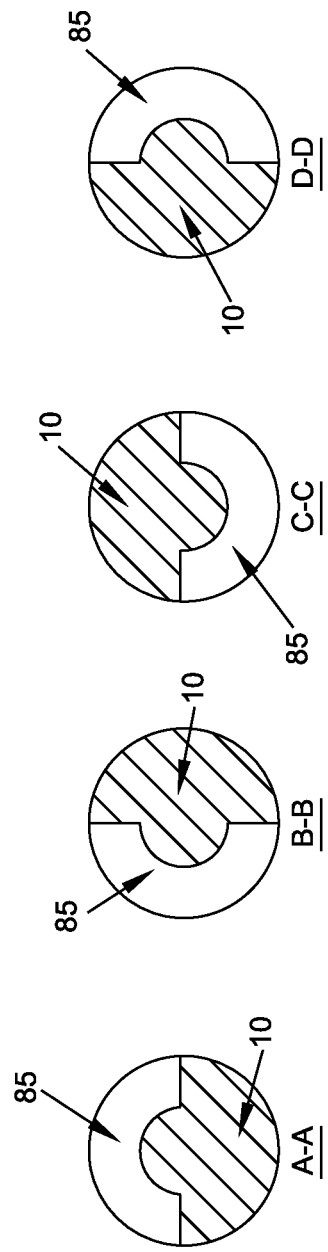
FIG. 15
FIG. 16
FIG. 17
FIG. 18
FIG. 19

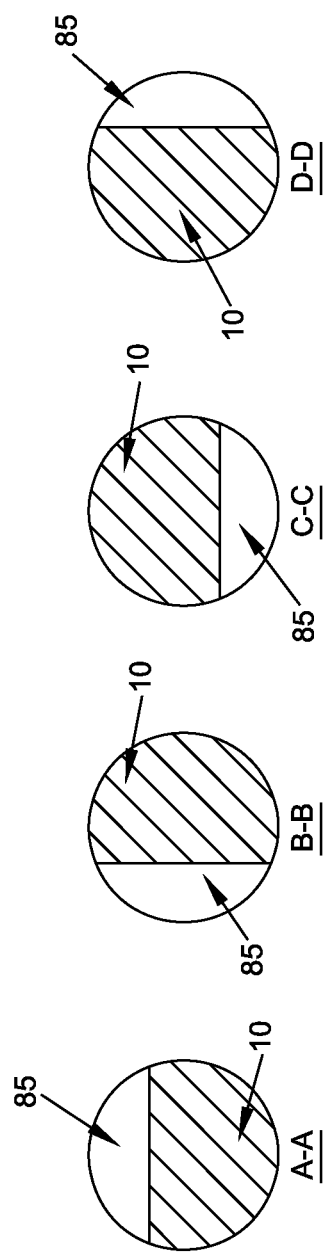

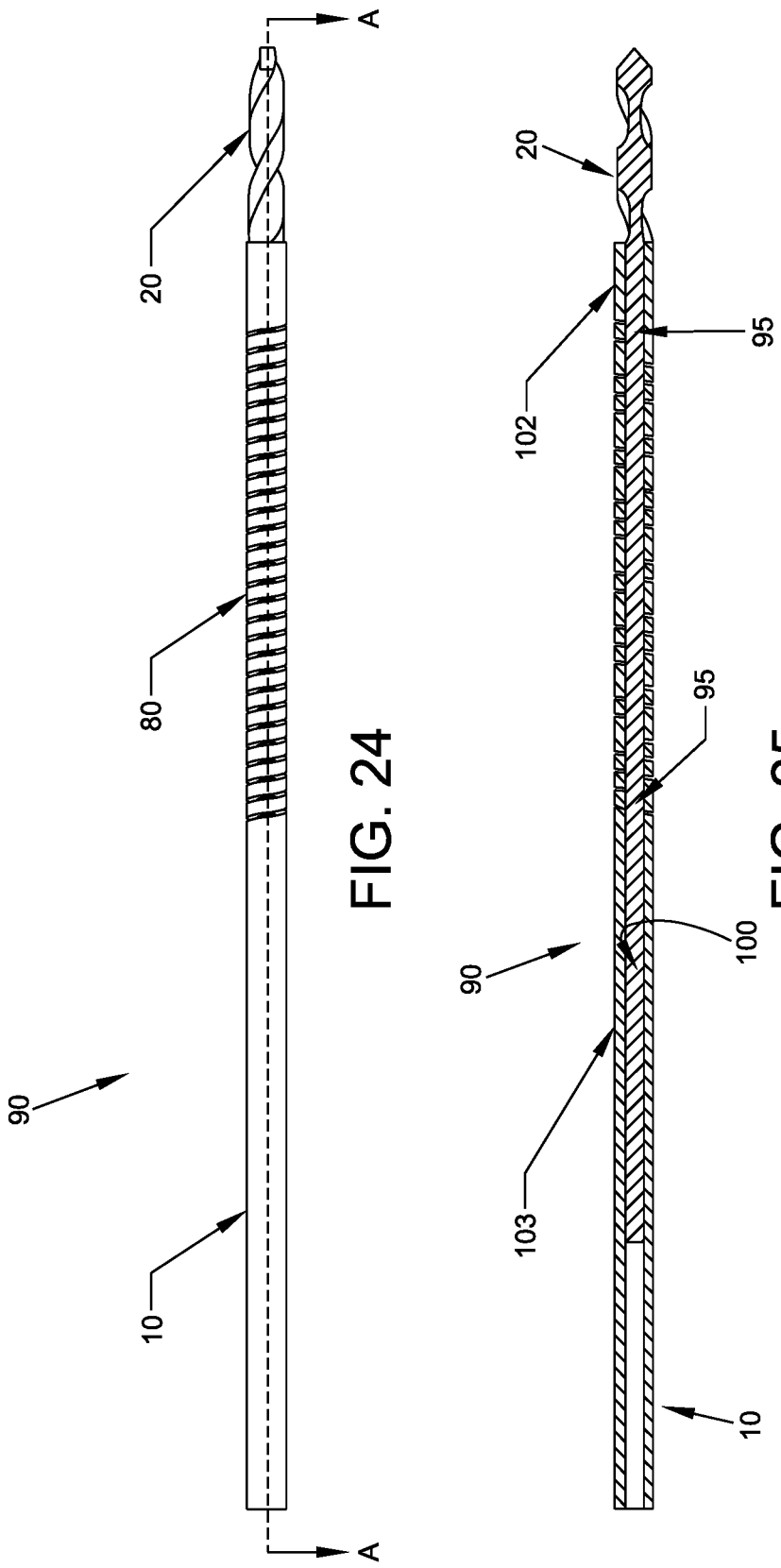

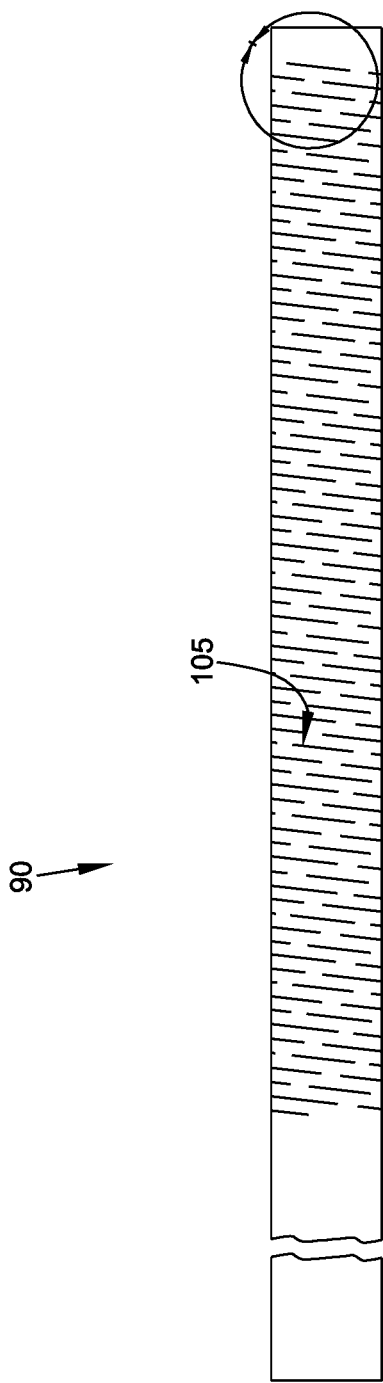
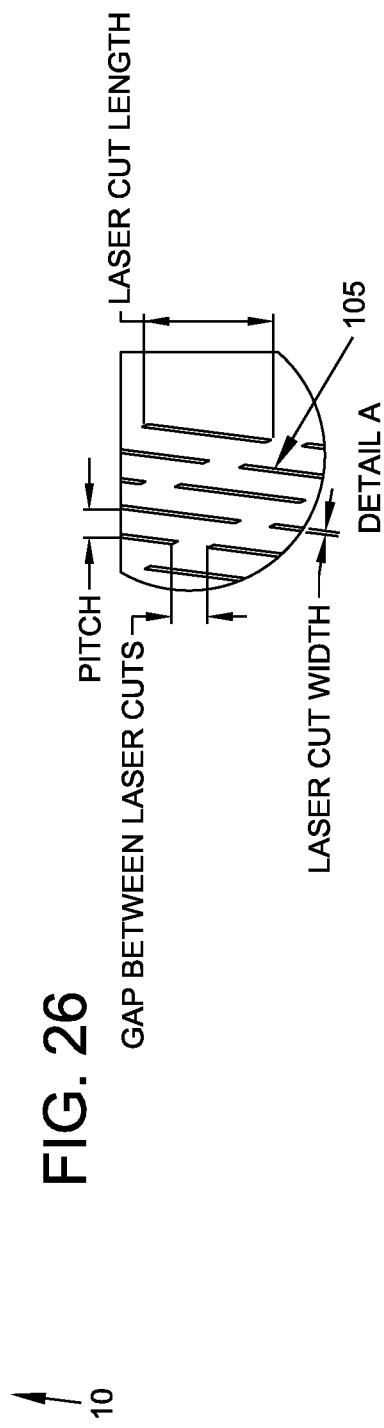

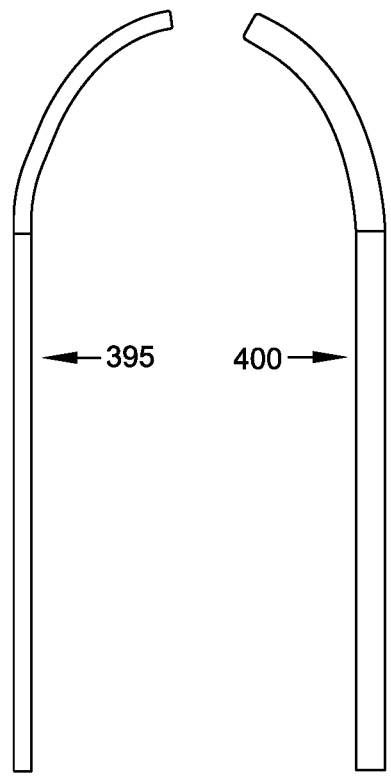
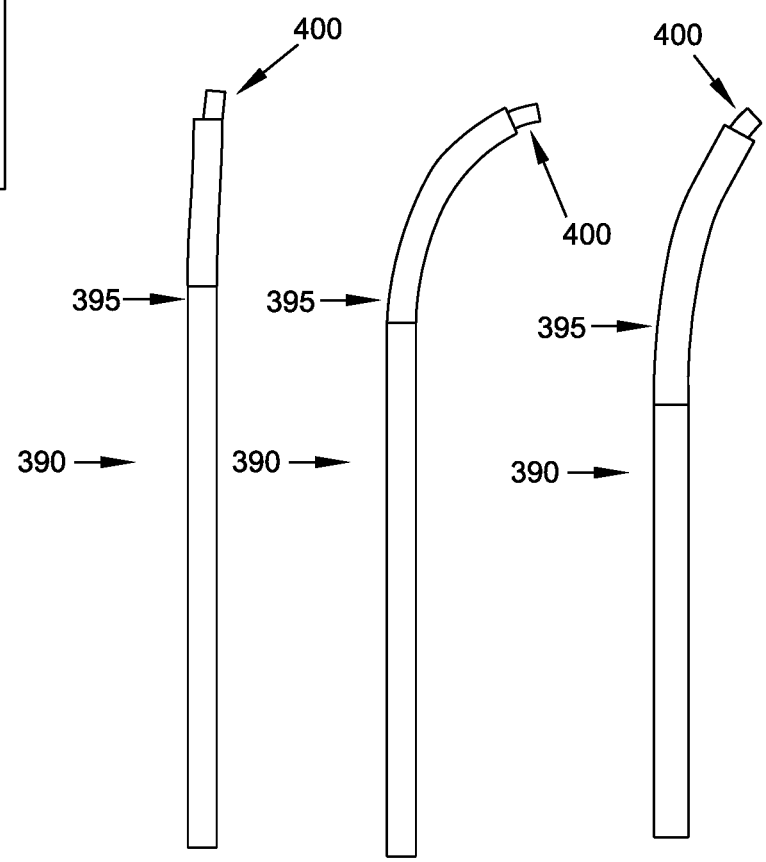
FIG. 47  FIG. 48  FIG. 49  FIG. 49A

DETAIL A

FLEXIBLE DRILL BIT AND ANGLED DRILL GUIDE FOR USE WITH THE SAME

REFERENCE TO PENDING PRIOR PATENT APPLICATIONS

This patent application is a continuation of pending prior U.S. patent application Ser. No. 13/764,565, filed Feb. 11, 2013 by Pivot Medical, Inc. for FLEXIBLE DRILL BIT AND ANGLED DRILL GUIDE FOR USE WITH THE SAME, which patent application in turn:

(i) is a continuation-in-part of pending prior U.S. patent application Ser. No. 13/735,806 filed Jan. 7, 2013 by J. Brook Burley et al. for FLEXIBLE DRILL BIT, which patent application claims benefit of prior U.S. Provisional Patent Application Ser. No. 61/583,265, filed Jan. 5, 2012 by J. Brook Burley et al. for FLEXIBLE DRILL BIT; and (ii) claims benefit of prior U.S. Provisional Patent Application Ser. No. 61/596,993, filed Feb. 9, 2012 by J. Brook Burley et al. for ANGLED DRILL GUIDE.

The four (4) above-identified patent applications are hereby incorporated herein by reference.

FIELD OF THE INVENTION

This invention relates to surgical methods and apparatus in general, and more particularly to methods and apparatus for drilling a hole in bone.

BACKGROUND OF THE INVENTION

The General Trend Toward Treating Joint Pathologies Using Minimally-Invasive, And Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require laying open the capsule of the shoulder joint. By way of further example but not limitation, it is also common to repair torn meniscal cartilage in the knee joint, and/or to replace ruptured ACL ligaments in the knee joint, using minimally-invasive, keyhole techniques.

While such minimally-invasive approaches can require additional training on the part of the surgeon, such procedures generally offer substantial advantages for the patient and have now become standard procedures for treating many shoulder joint and knee joint pathologies.

In addition to the foregoing, in view of the inherent advantages and widespread availability of minimally-invasive approaches for treating pathologies of the shoulder joint and the knee joint, the current trend is to provide such treatment much earlier in the lifecycle of the pathology, so as to address patient pain and so as to reduce the likelihood of exacerbating the pathology itself. This is in marked contrast to traditional surgical practices, which generally dictated postponing surgical procedures for as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and the knee joint. This is generally due to (i) the complex geometry of the hip joint itself, and (ii) the nature and location of the pathologies which are typically encountered in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is generally relatively difficult for surgeons to perform minimally-invasive procedures on the hip joint.

Furthermore, the pathways and approaches for entering the interior of the hip joint (i.e., the natural pathways which exist between adjacent bones and/or delicate neurovascular structures) are generally much more limited for the hip joint than for the shoulder joint or the knee joint. This limited access further complicates a surgeon's ability to effectively perform minimally-invasive procedures on the hip joint.

In addition to the foregoing, the nature and location of the pathologies of the hip joint also complicate a surgeon's ability to perform minimally-invasive procedures on the hip joint. By way of example but not limitation, consider a typical labrum tear or detachment in the hip joint. In this situation, instruments must generally be introduced into the joint space at an angle of approach which is offset from the angle at which the instrument addresses the joint anatomy. This makes drilling into bone, for example, a significantly more complicated procedure than in a case where the angle of approach is effectively aligned with the angle at which the instrument addresses the joint anatomy, such as is frequently the case in the shoulder joint. Furthermore, since the working space within the hip joint is typically extremely limited, it is even more difficult to properly adjust the alignment of surgical instruments (e.g., a drill) where the angle of approach is not aligned with the optimal angle for the instrument to address the joint anatomy.

As a result of the foregoing, minimally-invasive hip joint procedures are still relatively difficult to perform and hence less common in practice. Consequently, patients are typically forced to manage and endure their hip pain for as long as possible, until a resurfacing procedure or a partial or total hip replacement procedure can no longer be avoided. These resurfacing or replacement procedures are generally then performed as a highly-invasive, open procedure, replete with all of the disadvantages associated with highly-invasive, open procedures.

As a result, there is, in general, a pressing need for improved methods and apparatus for treating pathologies of the hip joint.

More particularly, there is a pressing need for improved methods and apparatus for introducing instruments into the joint space where the instruments will address the joint anatomy at an angle which is offset from the angle of approach. By way of example but not limitation, in some cases it may be desirable to drill into bone at an angle which is offset from the angle at which the drill is inserted into the joint space, in order to create a hole in the bone at an optimum location, e.g., at an optimum location to receive a suture anchor for use in effecting a labral repair.

SUMMARY OF THE PRESENT INVENTION

These and other objects of the present invention are addressed by the provision and use of a new flexible drill bit and an angled drill guide for use with the same, which may be used for drilling a hole in bone (or another material) where the flexible drill bit will enter the bone at an angle which is offset from the angle of approach.

The flexible drill bit and angled drill guide are particularly advantageous in situations where it is desirable to pass the drill bit into a joint in a curved configuration, such as where the drill bit is to be inserted into the joint through a curved guide or cannula.

In accordance with the present invention, the flexible drill bit is constructed so that it is flexible enough to bend into a curved state, yet strong enough to transmit the torsional forces required for drilling into bone (or another material).

And the angled drill guide is constructed so that it is able to support the flexible drill bit while the flexible drill bit is in its curved state and drilling into a target material (e.g., bone).

In one preferred form of the present invention, there is provided a flexible drill bit comprising:

a proximal shaft portion for connecting to a source of turning;

a distal cutting tip portion for boring into a material; and an intermediate shaft portion extending between the proximal shaft portion and the distal cutting tip portion, the intermediate shaft portion being characterized by (i) sufficient longitudinal flexibility so as to permit the flexible drill bit to be passed along a curve, and (ii) sufficient torsional strength to permit the flexible drill bit to bore into the material.

In another preferred form of the present invention, there is provided a method for forming a hole in a material, the method comprising: providing a flexible drill bit comprising:

a proximal shaft portion for connecting to a source of turning;

a distal cutting tip portion for boring into a material; and an intermediate shaft portion extending between the proximal shaft portion and the distal cutting tip portion, the intermediate shaft portion being characterized by (i) sufficient longitudinal flexibility so as to permit the flexible drill bit to be passed along a curve, and (ii) sufficient torsional strength to permit the flexible drill bit to bore into the material;

advancing the flexible drill bit to the material along a first angle of approach;

contacting the material at a second angle of approach; and turning the flexible drill bit so as to form a hole in the material.

In another preferred form of the present invention there is provided apparatus for drilling a hole in material, the apparatus comprising:

an angled drill guide comprising a curved distal section, a less-curved proximal section, and a lumen extending therebetween, wherein the less-curved proximal section comprises a flat extending therealong for reducing the effective diameter of the less-curved proximal section so as to minimize interference between the angled drill guide and the side wall of an access cannula.

In another preferred form of the present invention there is provided apparatus for drilling a hole in material, the apparatus comprising:

an angled drill guide comprising a curved distal section, a less-curved proximal section, and a lumen extending therebetween, wherein the curved distal section comprises first, second and third teeth extending distally therefrom, wherein the first tooth is set at the outer perimeter of the curve of the curved distal section, and wherein the second and third teeth are set at the inner perimeter of the curve of the curved distal section.

In another preferred form of the present invention there is provided apparatus for drilling a hole in material, the apparatus comprising:

an angled drill guide comprising a curved distal section, a less-curved proximal section, and a lumen extending therebetween, wherein the curved distal section comprises at least one window extending through the side wall thereof, and at least one side cut communicating with the at least one window and extending therefrom, so as to allow a user to view a flexible drill bit disposed within the lumen of the angled drill guide.

In another preferred form of the present invention there is provided apparatus for drilling a hole in material, the apparatus comprising:

an angled drill guide comprising a curved distal section, a less-curved proximal section, and a lumen extending therebetween, wherein the curved distal section comprises a dimple for effectively narrowing the lumen of the angled drill guide opposite to the curve of the angled drill guide, whereby to angularly re-align a flexible drill bit exiting the distal section of the angled drill guide.

In another preferred form of the present invention there is provided apparatus for drilling a hole in material, the apparatus comprising:

an angled drill guide comprising a curved distal section, a less-curved proximal section, and a lumen extending therebetween, wherein the lumen tapers inwardly in the curved distal section so as to re-center a flexible drill bit exiting the distal section of the angled drill guide.

In another preferred form of the present invention there is provided apparatus for drilling a hole in material, the apparatus comprising:

an angled drill guide comprising a curved distal section, a less-curved proximal section, and a lumen extending therebetween, wherein the curved distal section comprises compound curves so as to re-align a flexible drill bit exiting the distal section of the angled drill guide.

In another preferred form of the present invention there is provided apparatus for drilling a hole in material, the apparatus comprising:

an angled drill guide comprising a curved distal section, a less-curved proximal section, and a lumen extending therebetween; and a handle mounted to the angled drill guide so that the handle is offset from the longitudinal axis of the less-curved proximal section of the angled drill guide and aligned with the curved distal section of the angled drill guide, whereby to allow the user to push the distal end of the angled drill guide directly against the outer surface of the material which is to be drilled.

In another preferred form of the present invention there is provided apparatus for drilling a hole in material, the apparatus comprising:

an articulating angled drill guide comprising a curved inner sheath and a less-curved outer sheath, wherein the curved inner sheath is telescopically received within the less-curved outer sheath.

In another preferred form of the present invention there is provided apparatus for drilling a hole in material, the apparatus comprising:

an articulating angled drill guide comprising a curved inner sheath and a curved outer sheath, wherein the curved inner sheath is slidably received within the curved outer sheath.

In another preferred form of the present invention there is provided a friction-reducing flexible drill bit comprising a flexible drill bit having a low friction coating formed thereon.

In another preferred form of the present invention there is provided a method for drilling a hole in material, the method comprising:

providing an angled drill guide comprising a curved distal section, a less-curved proximal section, and a lumen extending therebetween, wherein the less-curved proximal section comprises a flat extending therealong for reducing the effective diameter of the less-curved proximal section so as to minimize interference between the angled drill guide and the side wall of an access cannula;

positioning the angled drill guide against the material to be drilled; and advancing a flexible drill bit through the angled drill guide and drilling into the material.

In another preferred form of the present invention there is provided a method for drilling a hole in material, the method comprising:

providing an angled drill guide comprising a curved distal section, a less-curved proximal section, and a lumen extending therebetween, wherein the curved distal section comprises first, second and third teeth extending distally therefrom, wherein the first tooth is set at the outer perimeter of the curve of the curved distal section, and wherein the second and third teeth are set at the inner perimeter of the curve of the curved distal section;

positioning the angled drill guide against the material to be drilled; and advancing a flexible drill bit through the angled drill guide and drilling into the material.

In another preferred form of the present invention there is provided a method for drilling a hole in material, the method comprising:

providing an angled drill guide comprising a curved distal section, a less-curved proximal section, and a lumen extending therebetween, wherein the curved distal section comprises at least one window extending through the side wall thereof, and at least one side cut communicating with the at least one window and extending therefrom, so as to allow a user to view a flexible drill bit disposed within the lumen of the angled drill guide;

positioning the angled drill guide against the material to be drilled; and advancing a flexible drill bit through the angled drill guide and drilling into the material.

In another preferred form of the present invention there is provided a method for drilling a hole in material, the method comprising:

providing an angled drill guide comprising a curved distal section, a less-curved proximal section, and a lumen extending therebetween, wherein the curved distal section comprises a dimple for effectively narrowing the lumen of the angled drill guide opposite to the curve of the angled drill guide, whereby to angularly re-align a flexible drill bit exiting the distal section of the angled drill guide;

positioning the angled drill guide against the material to be drilled; and advancing a flexible drill bit through the angled drill guide and drilling into the material.

In another preferred form of the present invention there is provided a method for drilling a hole in material, the method comprising:

providing an angled drill guide comprising a curved distal section, a less-curved proximal section, and a lumen extending therebetween; and a handle mounted to the angled drill guide so that the handle is offset from the longitudinal axis of the less-curved proximal section of the angled drill guide and aligned with the curved distal section of the angled drill guide, whereby to allow the user to push the distal end of the angled drill guide directly against the outer surface of the material which is to be drilled;

positioning the angled drill guide against the material to be drilled; and advancing a flexible drill bit through the angled drill guide and drilling into the material.

In another preferred form of the present invention there is provided a method for drilling a hole in material, the method comprising:

providing an articulating angled drill guide comprising a curved inner sheath and a less-curved outer sheath, wherein the curved inner sheath is telescopically received within the less-curved outer sheath;

positioning the angled drill guide against the material to be drilled; and advancing a flexible drill bit through the angled drill guide and drilling into the material.

In another preferred form of the present invention there is provided a method for drilling a hole in material, the method comprising:

providing an articulating angled drill guide comprising a curved inner sheath and a curved outer sheath, wherein the curved inner sheath is slidably received within the curved outer sheath;

positioning the angled drill guide against the material to be drilled; and advancing a flexible drill bit through the angled drill guide and drilling into the material.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 15 is a schematic view showing still another form of flexible drill bit formed in accordance with the present invention;

FIGS. 16-19 are schematic cross-sectional views taken along lines A-A, B-B, C-C and D-D, respectively, of FIG. 15 in one form of the invention;

FIGS. 20-23 are schematic cross-sectional views taken along lines A-A, B-B, C-C and D-D, respectively, of FIG. 15 in another form of the invention;

FIG. 24 is a schematic view showing another form of flexible drill bit formed in accordance with the present invention;

FIG. 25 is a schematic cross-sectional view taken along line A-A of FIG. 24;

FIG. 26 is a schematic view showing still another form of flexible drill bit formed in accordance with the present invention;

FIG. 27 is an enlarged schematic view showing selected portions of the flexible drill bit of FIG. 26;

FIGS. 47-49 and 49A are schematic views showing still another novel articulating angled drill guide formed in accordance with the present invention;

DETAILED DESCRIPTION OF THE PREFERRED EMBODIMENTS

Flexible Drill Bit Having a "Unibody" Construction

Figure 1:
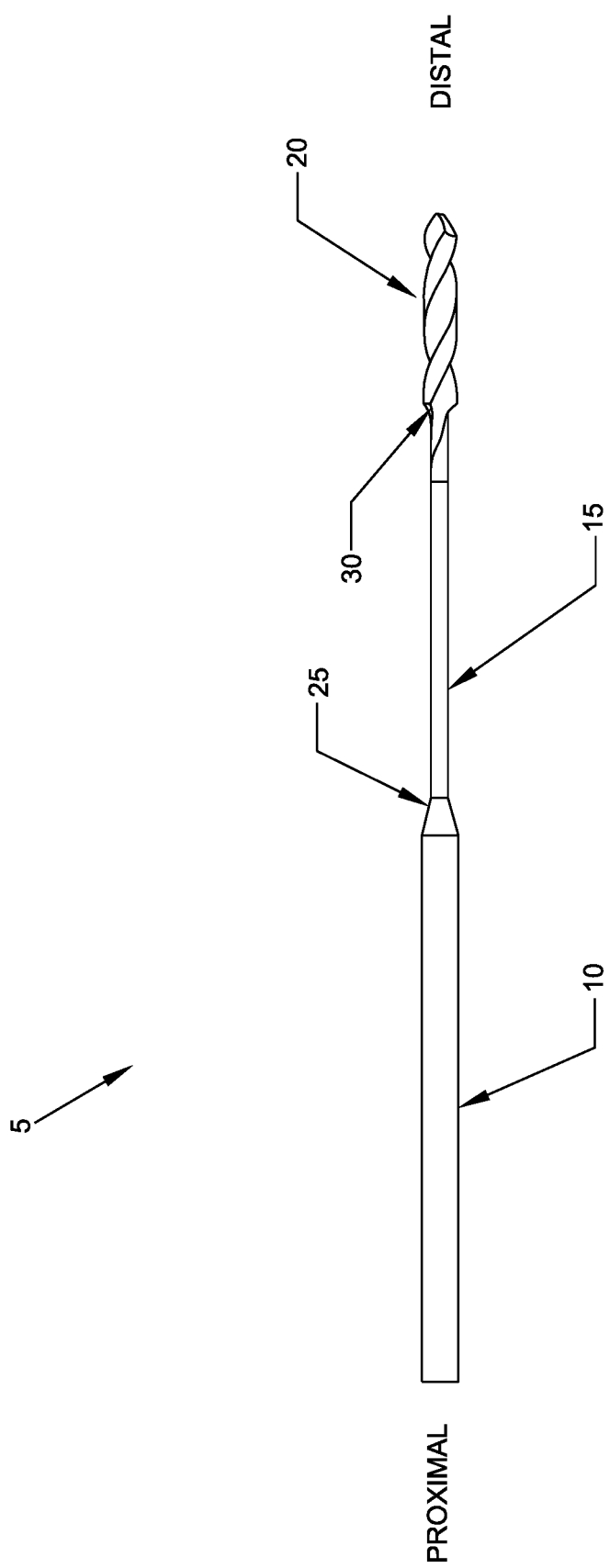
FIG. 1 is a schematic view showing a flexible drill bit formed in accordance with the present invention.
Figure 2:
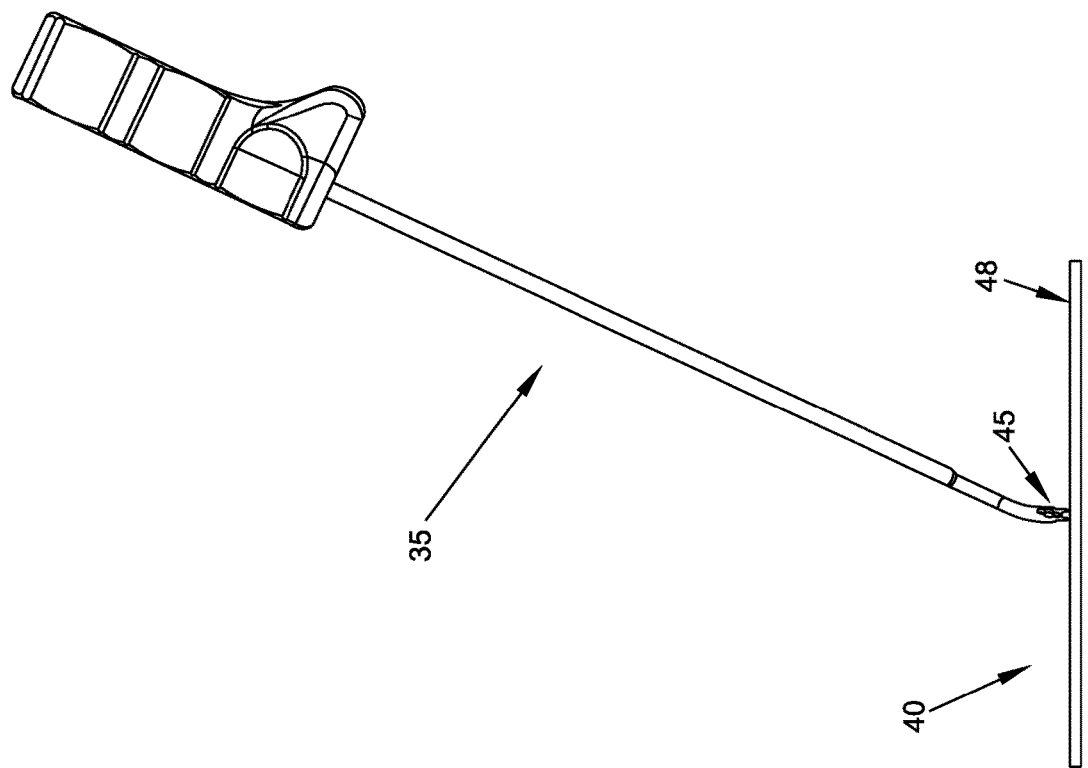
FIGS. 2-5 are schematic views showing the flexible drill bit of FIG. 1 being used in conjunction with a curved drill guide to form a hole in bone.
Figure 3:
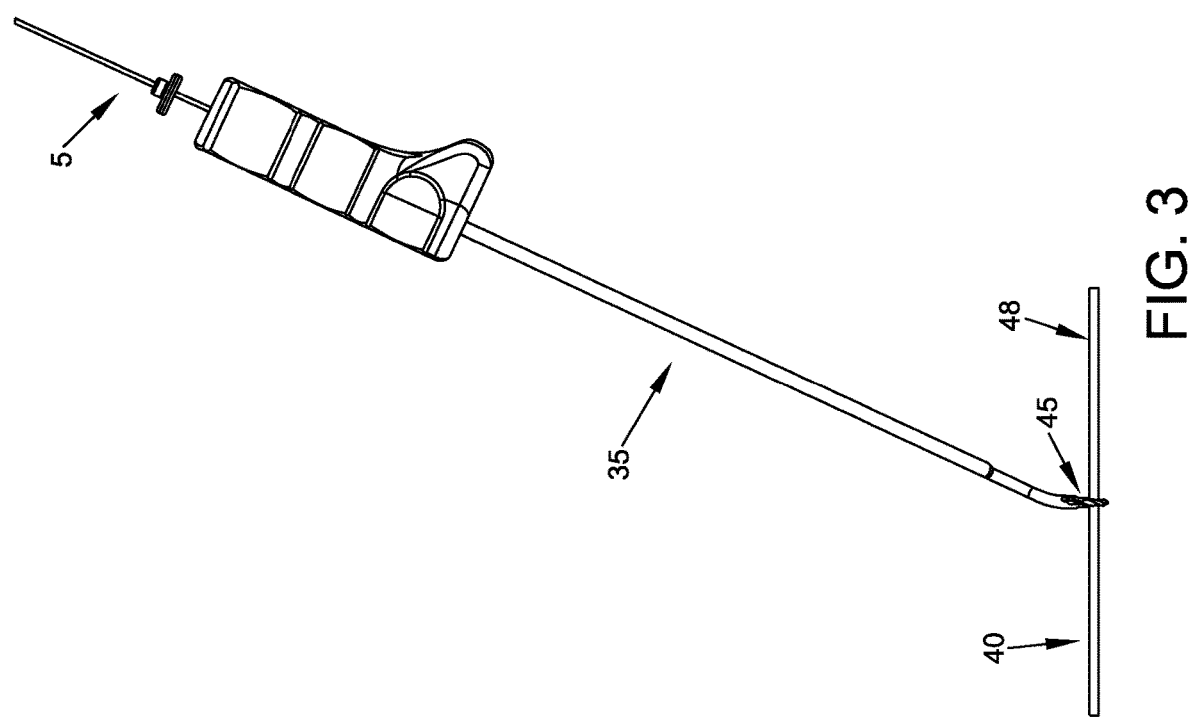
Figure 4:
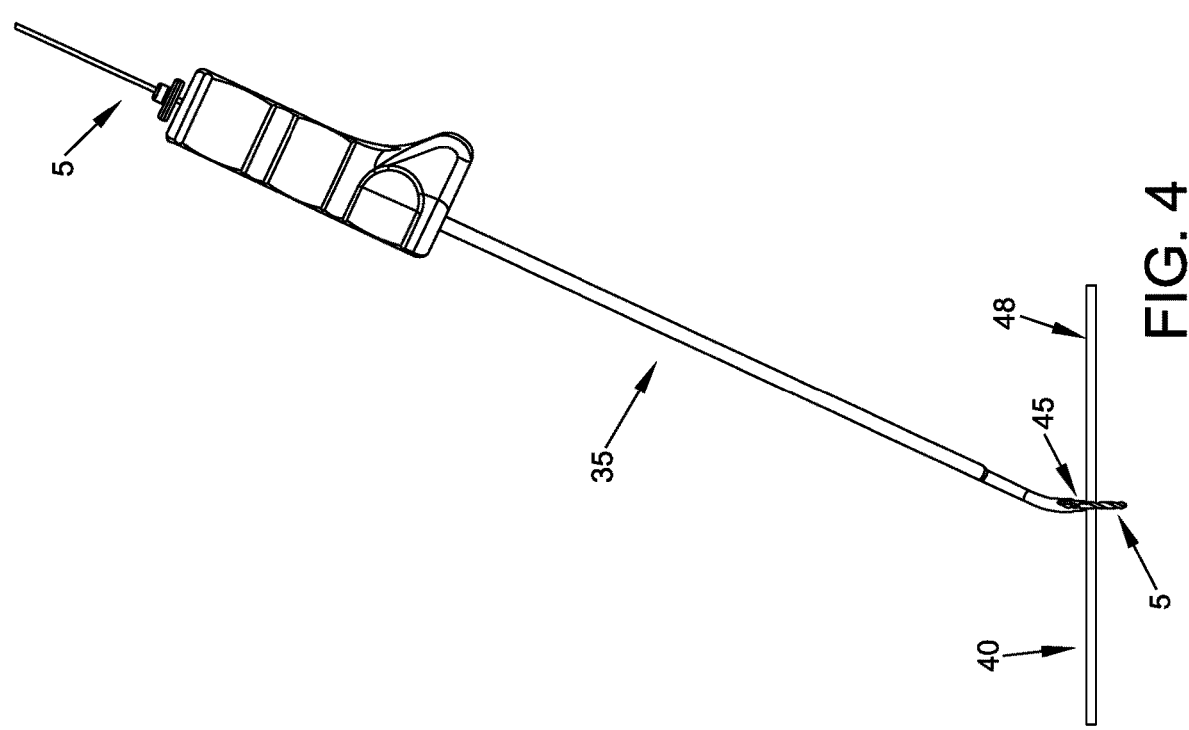

Looking first at FIG. 1, there is a shown a flexible drill bit 5 formed in accordance with the present invention. Flexible drill bit 5 comprises three sections, i.e., a full diameter shaft portion 10, a reduced diameter shaft portion 15, and a fluted cutting tip portion 20. Full diameter shaft portion 10, reduced diameter shaft portion 15, and fluted cutting tip portion 20 are all formed integral with one another so as to create a flexible drill bit having a "unibody" construction. If desired, a transition area 25 may be formed between full diameter shaft portion 10 and reduced diameter shaft portion 15, and/or a transition area 30 may be formed between reduced diameter shaft portion 15 and fluted cutting tip portion 20.

The "unibody" construction eliminates the need for a mechanical joint connecting the cutting tip of the flexible drill bit (e.g., fluted cutting tip portion 20) to the flexible portion of the flexible drill bit (e.g., reduced diameter shaft portion 15), thereby eliminating a possible point of failure. Such a failure of a mechanical joint can be particularly problematic if the mechanical joint were to fail below the surface of the bone (i.e., subchondral); in this scenario, it would be unlikely that the portion of the drill bit left in the bone could be recovered. Thus, the possible failure of such a mechanical joint creates a serious clinical concern. In addition, the "unibody" construction eliminates the need for a mechanical joint connecting the flexible portion of the flexible drill bit (e.g., reduced diameter shaft portion 15) to the full diameter shaft portion (e.g., full diameter shaft portion 10) of the flexible drill bit, thus eliminating another possible point of failure.

The flexible drill bit may comprise a material such as Nitinol, stainless steel, titanium, or other appropriate material, but is preferably Nitinol.

The reduced diameter shaft portion 15 of flexible drill bit 5 provides flexibility in that portion of the drill bit while still providing the torsional strength needed to drill into bone. The diameter of the reduced diameter shaft portion 15 is preferably approximately 20-40% smaller than the diameter of the full diameter shaft portion 10, and more preferably approximately 25% smaller than the diameter of the full diameter shaft portion 10.

The transition area 30 located between fluted cutting tip portion 20 and the reduced diameter shaft portion 15, and/or the transition area 25 located between the reduced diameter shaft portion 15 and the full diameter shaft portion 10, are preferably formed so as to distribute stress, whereby to minimize the possibility of mechanical failure at the transition areas.

Full diameter shaft portion 10 provides a region, preferably at its proximal end, in which flexible drill bit 5 can be attached to a drill.

Fluted cutting tip portion 20 is preferably sufficiently rigid to form a straight hole in the target bone. To that end, the length of fluted cutting tip portion 20 must be short enough so that the fluted cutting tip portion 20 may pass through the curve of a curved drill guide or curved cannula. In one preferred embodiment, fluted cutting tip portion 20 has a length which is approximately 6 times greater than its diameter.

FIGS. 2-5 show flexible drill bit 5 being used in conjunction with a curved drill guide 35 to form a hole in a bone 40. More particularly, as seen in the figures, the distal tip 45 of curved drill guide 35 is placed against the outer surface 48 of bone 40, and then flexible drill bit 5 is passed through the lumen 50 of curved drill guide 35 and directed into bone 40 so as to make the hole in the bone at the desired location and with the desired angle.

Figure 5:
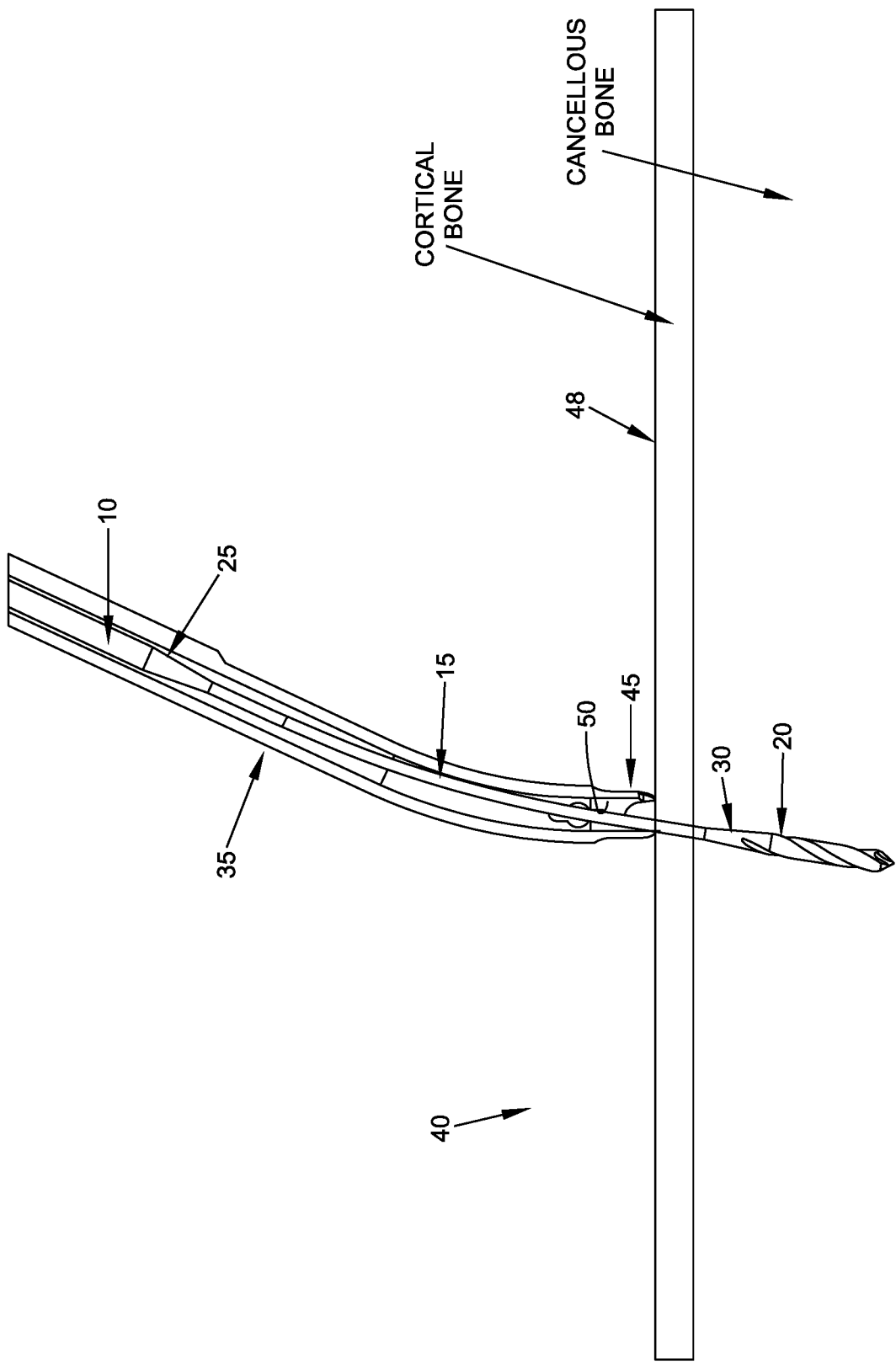

Note in FIG. 5 how the curvature of curved drill guide 35 can combine with the differences in the diameters of the reduced diameter shaft portion 15 and lumen 50 so as to result in a non-perpendicular entry of flexible drill bit 5 into the bone, even where distal tip 45 of curved drill guide 35 is disposed substantially perpendicular to outer surface 48 of the bone. In other words, the curvature of curved drill guide 35 can combine with the differences in the diameters of reduced diameter shaft portion 15 and lumen 50 so that fluted cutting tip portion 20 is not perfectly coaxial with lumen 50 as fluted cutting tip portion 20 emerges from the distal end of curved drill guide 35. It will be apparent to one skilled in the art that, depending on the bone surface contour and/or the angle of approach of curved drill guide 35, the curved drill guide 35 may not always be disposed perpendicular to outer surface 48 of the bone. In this scenario, it is typically still desirable to have the fluted cutting tip portion 20 centered and aligned with the end of the curved drill guide 35.

Figure 6:
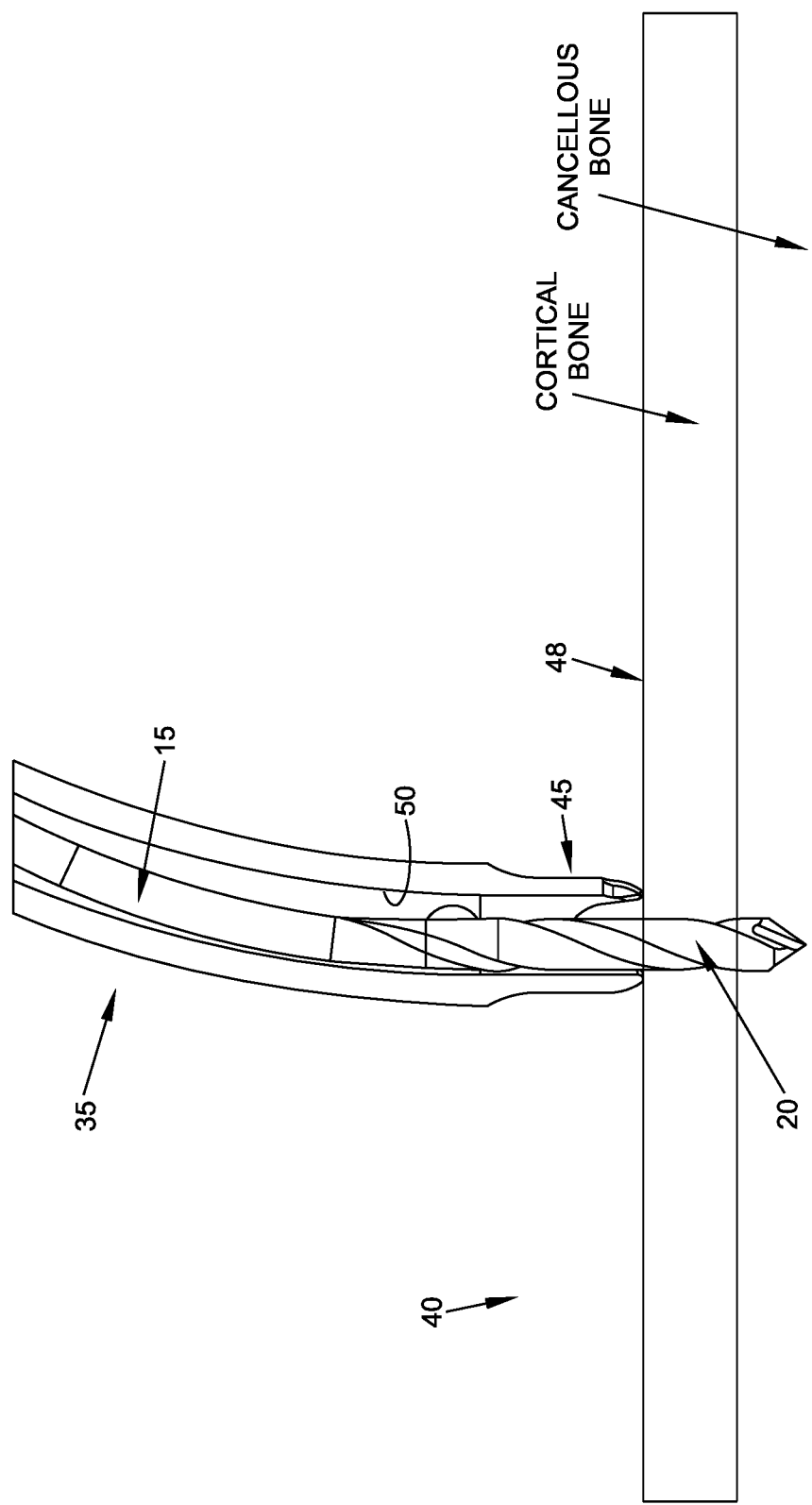
FIGS. 6 and 7 are schematic views showing another flexible drill bit formed in accordance with the present invention and being used in conjunction with a curved drill guide to form a hole in bone.
Figure 7:
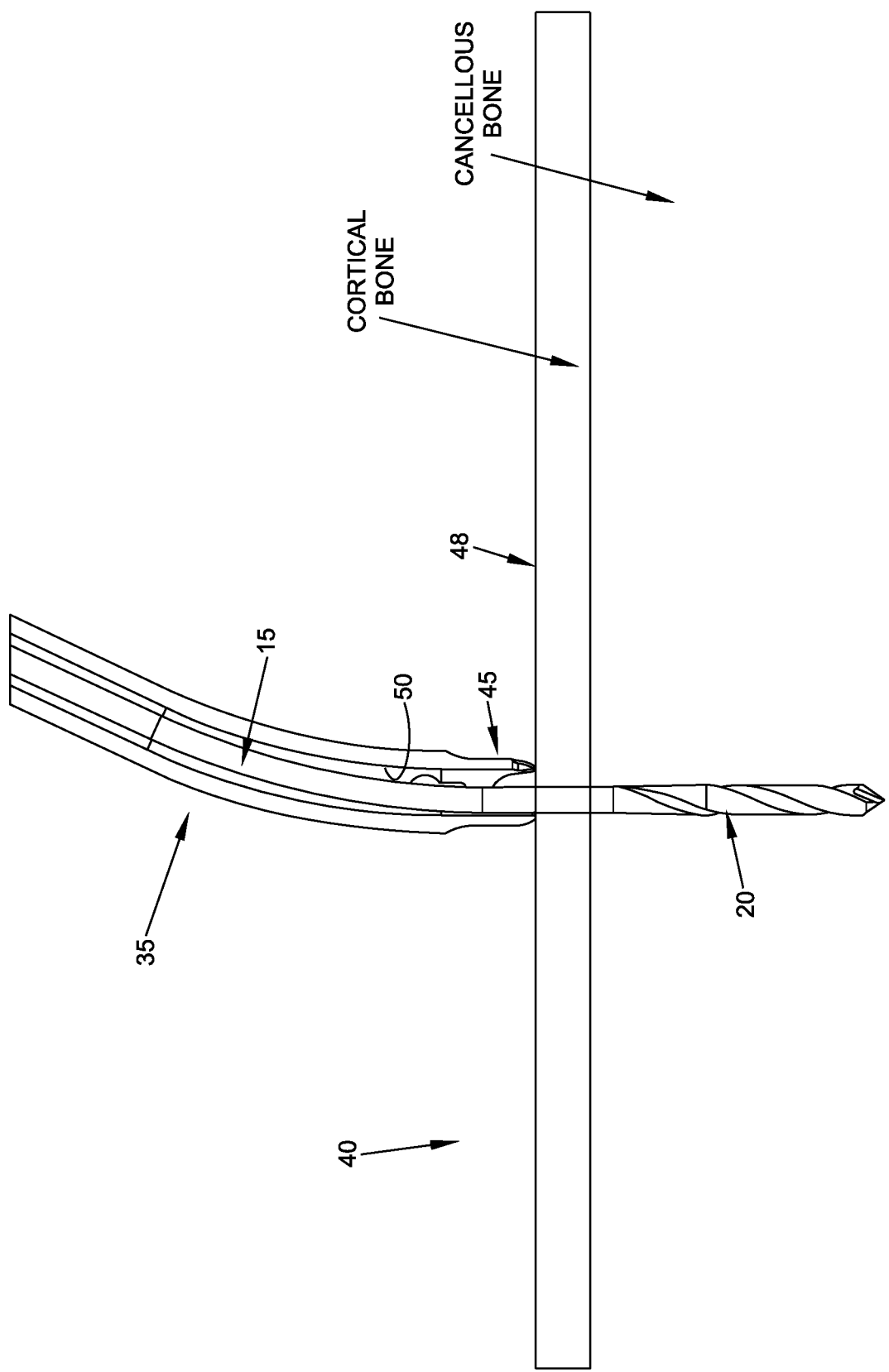

FIGS. 6 and 7 show another form of the invention where the diameter of reduced diameter shaft portion 15 is sized so as to be closer to the diameter of fluted cutting tip portion 20 and so as to be somewhat closer to the diameter of lumen 50 of curved drill guide 35. In this form of the invention, flexible drill bit 5 will tend to enter the bone closer to perpendicular. In other words, in this form of the invention, fluted cutting tip portion 20 will tend to remain more coaxial with lumen 50 as fluted cutting tip portion 20 emerges from the distal end of curved drill guide 35.

In one preferred form of the invention, full diameter shaft portion 10 has a length of approximately 12 inches and a diameter of approximately 0.063 inch; reduced diameter shaft portion 15 has a length of approximately 1.5 inches and a diameter of approximately 0.047 inch; fluted cutting tip portion 20 has a length of approximately 0.325 inch and a diameter of approximately 0.055 inch; and curved drill guide 35 has a radius of curvature of approximately 1.25 inches, a curve of approximately 25 degrees, and a lumen diameter of approximately 0.071 inch. In this preferred form of the invention, flexible drill bit 5 is capable of transmitting at least approximately 2 in-lbs (inch-pounds) of torque without failure, and more preferably approximately 3 in-lbs (inch-pounds) of torque without failure.

Figure 8:
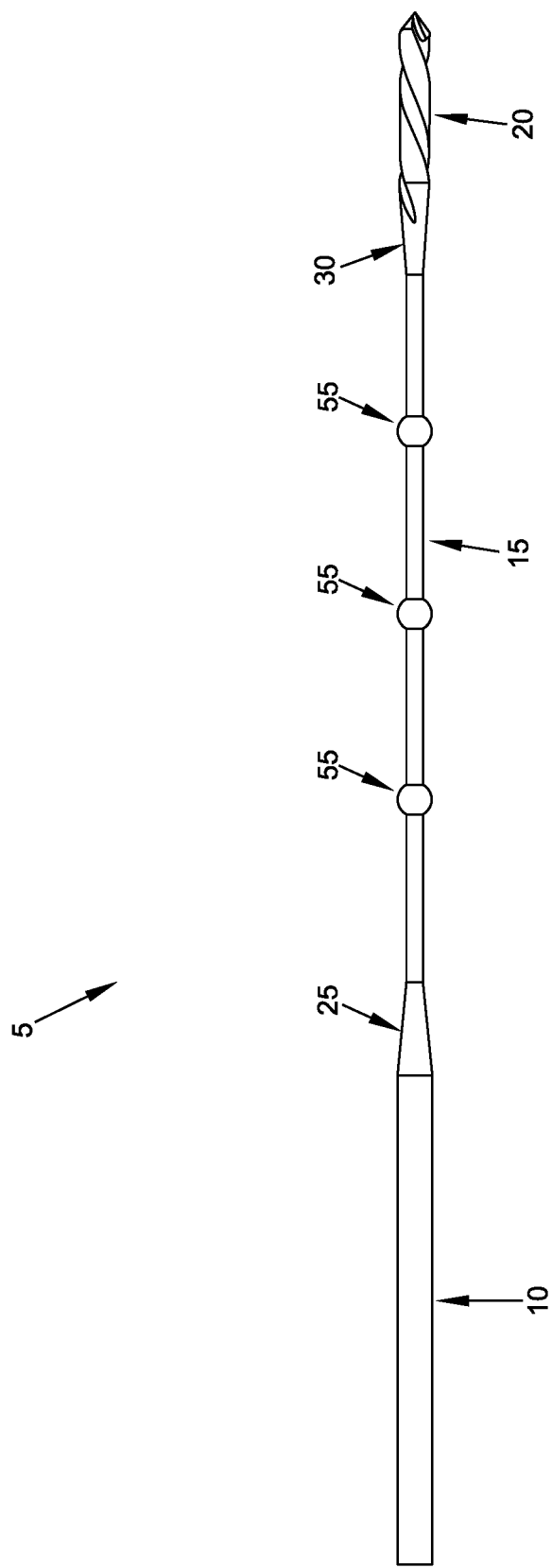
FIG. 8 is a schematic view showing still another flexible drill bit formed in accordance with the present invention.
Figure 9:
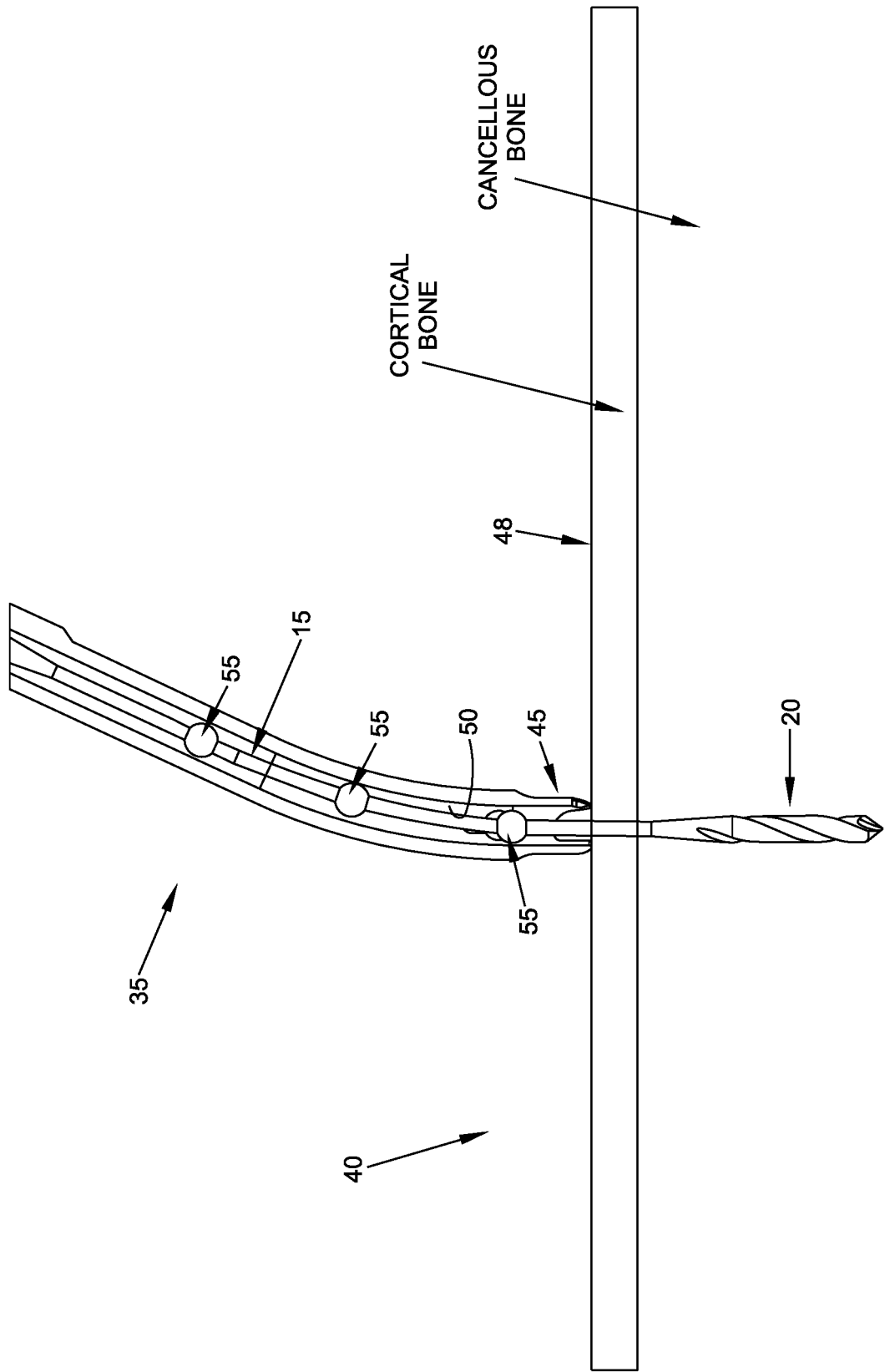
FIG. 9 is a schematic view showing the flexible drill bit of FIG. 8 being used in conjunction with a curved drill guide to form a hole in bone.

In another form of the invention, and looking now at FIGS. 8 and 9, one or more enlargements 55 may be formed on the reduced diameter shaft portion 15 of flexible drill bit 5. Enlargements 55 serve to keep flexible drill bit 5 centered in lumen 50 of curved drill guide 35 even where reduced diameter shaft portion 15 has a diameter which is significantly less than the diameter of lumen 50 of curved drill guide 35. In this form of the invention, enlargements 55 will also keep flexible drill bit 5 closer to perpendicular as it enters bone 40. In other words, in this form of the invention, fluted cutting tip portion 20 will tend to remain more coaxial with lumen 50 as fluted cutting tip portion 20 emerges from the distal end of curved drill guide 35.

Figure 10:
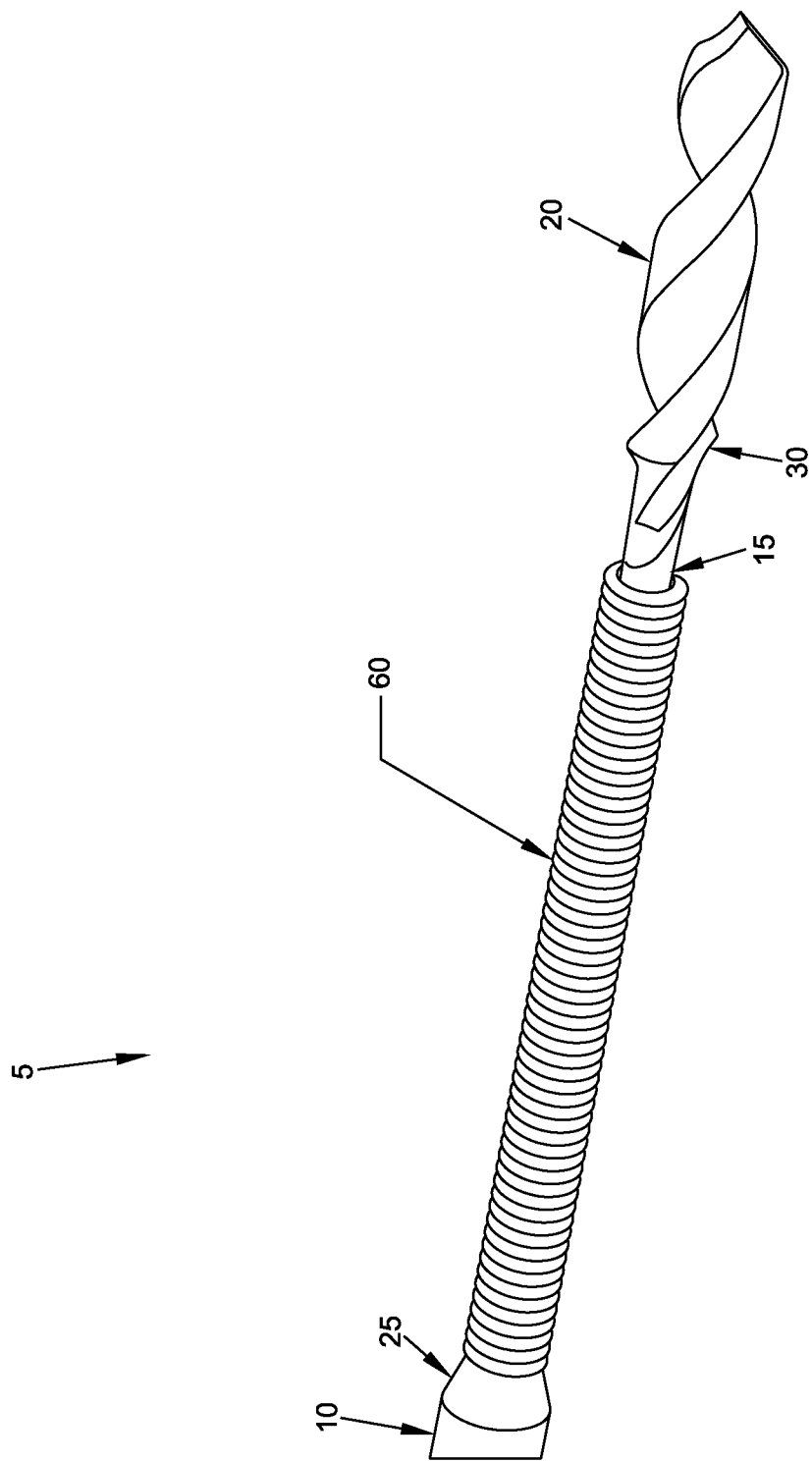
FIG. 10 is a schematic view showing the flexible drill bit of FIG. 1 with a helical coil disposed over a portion of the flexible drill bit.

In another embodiment, and looking now at FIG. 10, a helical coil 60 may be positioned over reduced diameter shaft portion 15 of flexible drill bit 5 so as to supplement the torque needed to drill into bone while still providing the flexibility needed to maneuver around a curve in a curved drill guide (e.g., curved drill guide 35) or curved cannula. Helical coil 60 also helps to keep flexible drill bit 5 centered in a curved drill guide (e.g., curved drill guide 35) and reduce the "mismatch" angle between flexible drill bit 5 and end of curved drill guide 35.

More particularly, helical coil 60 provides additional torsional strength and increased diameter to the reduced diameter shaft portion 15 of flexible drill bit 5 without significantly reducing the flexibility of the drill bit. The increased diameter of reduced diameter shaft portion 15 of flexible drill bit 5 (due to the presence of helical coil 60) creates a close fit within the drill guide or cannula, thereby ensuring that the drill bit remains coaxial with the curved drill guide or curved cannula as the flexible drill bit emerges from the distal end of the curved drill guide or curved cannula and engages the bone (or other material) which is being drilled.

Helical coil 60 may form a close fit around reduced diameter shaft portion 15 and be sized so that it rests between transition area 25 and transition area 30. Helical coil 60 may be resilient and may be stretched slightly (in its diameter) from its unbiased condition so as to allow the helical coil to be positioned onto reduced diameter shaft portion 15; in other words, in a free condition, the helical coil 60 has an inner diameter which is smaller than the outer diameter of the reduced diameter shaft portion 15. Helical coil 60 may simply sit on reduced diameter shaft portion 15, or it may be secured to reduced diameter shaft portion 15 (e.g., at one end of helical coil 60, at both ends of helical coil 60, and/or intermediate helical coil 60, etc.). In one preferred embodiment, helical coil 60 is secured at both its ends to reduced diameter shaft portion 15 and forms a close fit with reduced diameter shaft portion 15 or is stretched slightly diametrically from its unbiased condition onto reduced diameter shaft portion 15. Helical coil 60 may be secured to reduced diameter shaft portion 15 by soldering, adhesive, welding, mechanical interlock, or other appropriate attachment means. Helical coil 60 is preferably formed and positioned so that when the flexible drill bit is used to drill into bone, the helical coil will tighten onto reduced diameter shaft portion 15 during drilling. For example, if a flexible drill bit 5 rotates in a clockwise direction (when viewed from proximal to distal), the helical coil should have a counter-clockwise winding direction (again, when viewed from proximal to distal). This arrangement provides a preferred transfer of torque between reduced diameter shaft portion 15 and helical coil 60.

Helical coil 60 may comprise a material such as stainless steel, Nitinol or other suitable material. Helical coil 60 may comprise a wire of round or rectangular cross-section. Although FIG. 10 depicts a closely wound helical coil (i.e., with substantially no space between the coils), an alternative embodiment comprises spacing between the coils.

Figure 11:
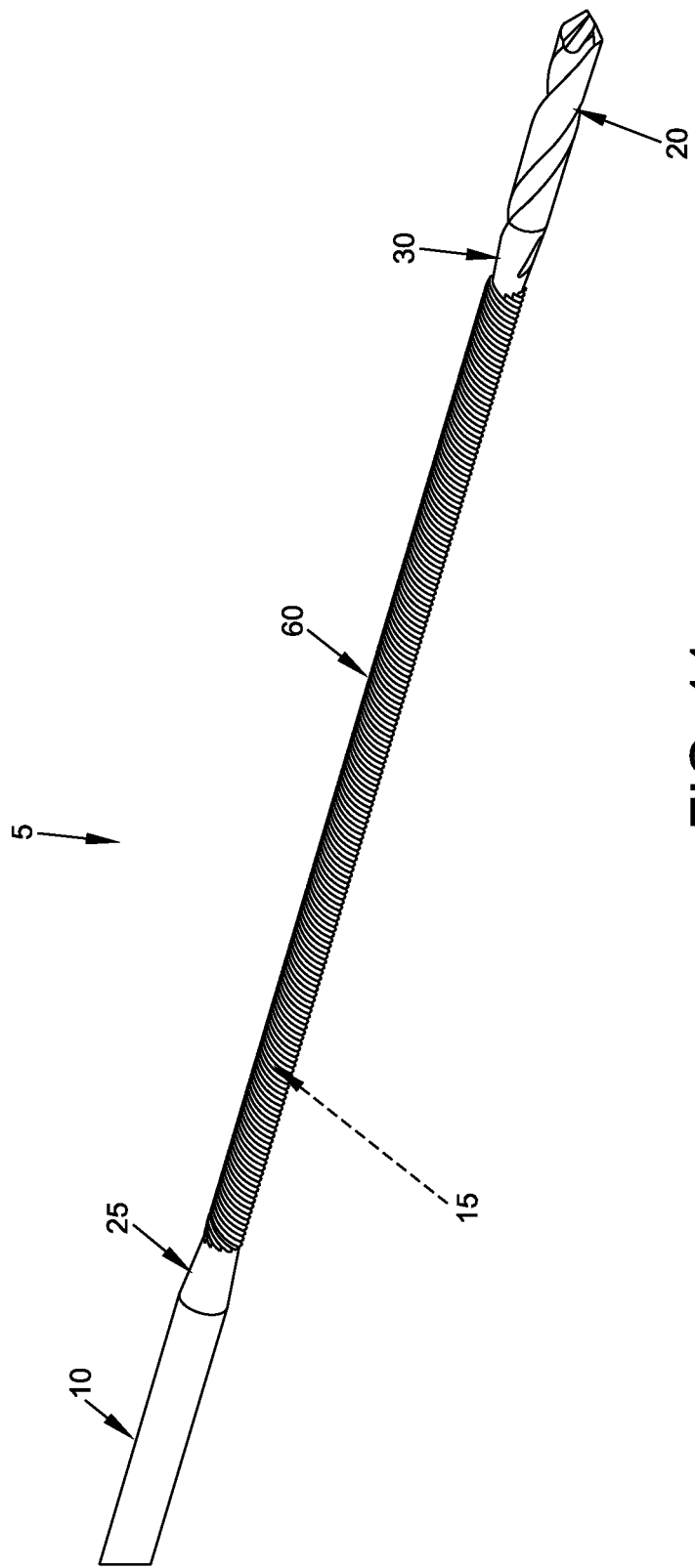
FIG. 11 is a schematic view showing the flexible drill bit of FIG. 1 with another form of helical coil disposed over a portion of the flexible drill bit.

FIG. 11 shows a construction similar to that of FIG. 10, except that helical coil 60 comprises a multi-strand coil (i.e., multiple strands are coiled together). In this embodiment, adjacent multiple strands follow the same coil pitch. However, even with coils touching each other, the pitch can be greater than a single strand arrangement (e.g., as shown in FIG. 10). This construction (i.e., larger pitch with coils touching) can be beneficial to reduce "play" in the coil; that is, as the flexible drill bit 5 starts drilling into bone, the helical coil 60 will more quickly respond in carrying a portion of the torque.

Figure 12:
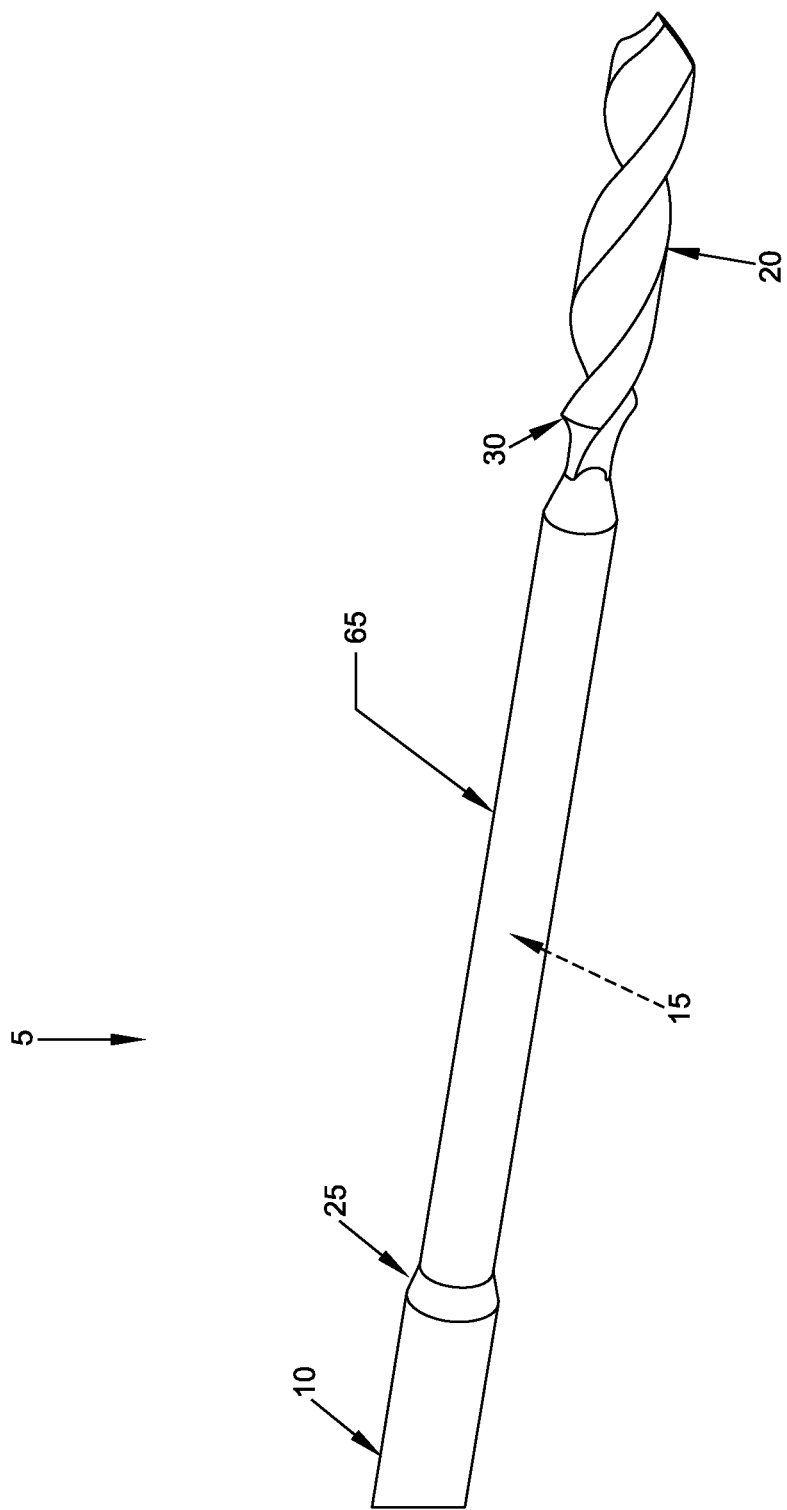
FIG. 12 is a schematic view showing the flexible drill bit of FIG. 1 with an over-molded sheath disposed over a portion of the flexible drill bit.

In another embodiment, and looking now at FIG. 12, an over-molded sheath 65 may be positioned over reduced diameter shaft portion 15 of flexible drill bit 5. Over-molded sheath 65 provides reduced friction (e.g., with curved drill guide 35 and/or bone 40) and increased diameter to reduced diameter shaft portion 15 of flexible drill bit 5, while still enabling bending of the reduced diameter shaft portion 15 of flexible drill bit 5. Over-molded sheath 65 may comprise a polymer such as Nylon or polytetrafluoroethylene (PTFE). Over-molded sheath 65 may be over-molded onto reduced diameter shaft portion 15 by injection molding or by diameter reduction (e.g., by shrinking or melting over-molded sheath 65 onto reduced diameter shaft portion 15).

Figure 13:
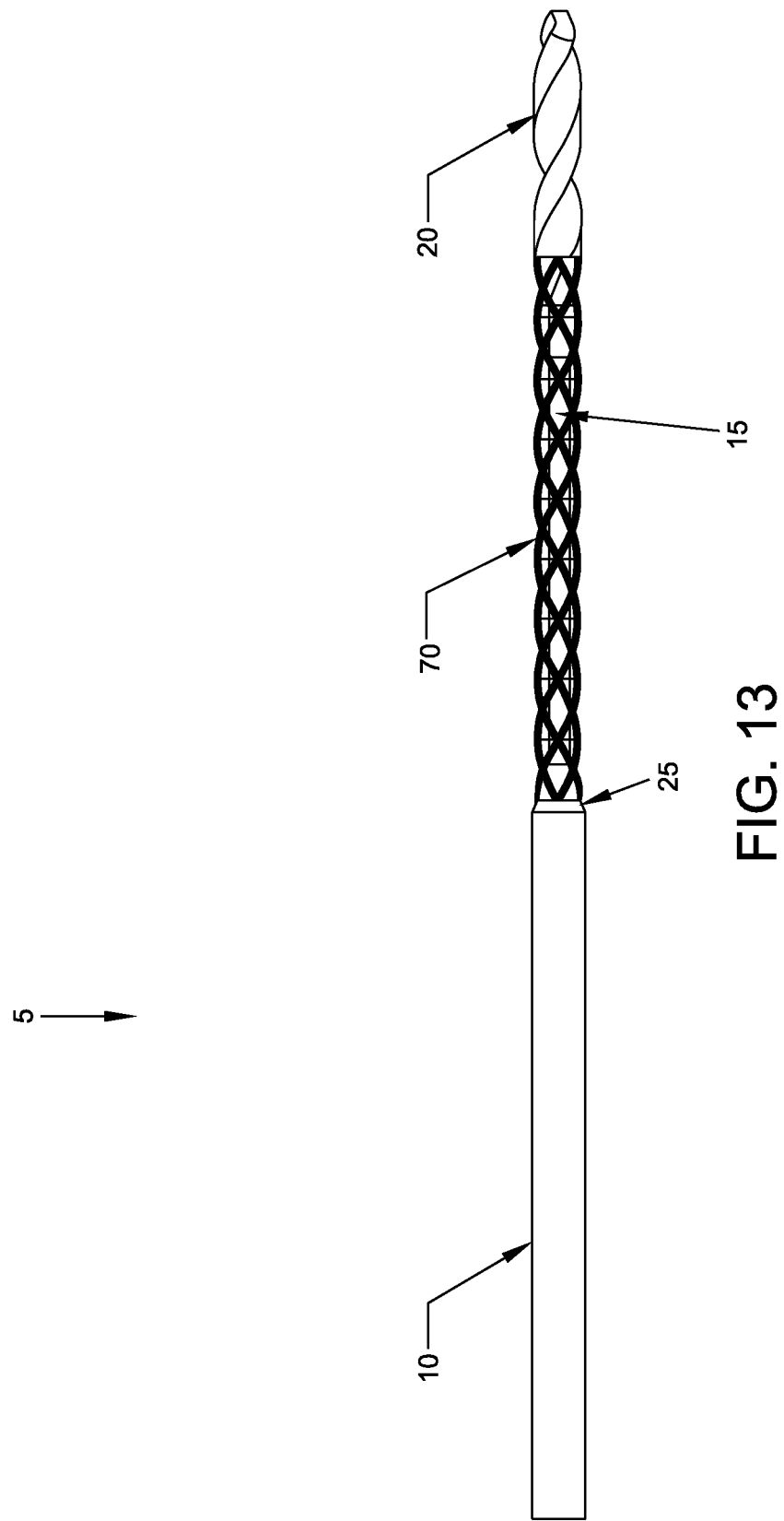
FIG. 13 is a schematic view showing the flexible drill bit of FIG. 1 with a metal braid or mesh disposed over a portion of the flexible drill bit.

In another embodiment, and looking now at FIG. 13, a braid or mesh 70 (preferably but not necessarily formed out of metal) may be positioned over reduced diameter shaft portion 15 of flexible drill bit 5. Metal braid or mesh 70 provides torsional strength and increased diameter to reduced diameter shaft portion 15 of flexible drill bit 5, while still enabling bending/flexing of reduced diameter shaft portion 15 of flexible drill bit 5. Metal braid or mesh 70 may comprise a material such as stainless steel or Nitinol. It may comprise wire having a rectangular cross-section. Metal braid or mesh 70 may be attached to reduced diameter shaft portion 15 of flexible drill bit 5 by attaching one or both of its ends to the reduced diameter shaft portion, or by attaching an intermediate portion of metal braid or mesh 70 to reduced diameter shaft portion 15, or both (e.g., by welding, adhesive, etc.). Alternatively, or additionally, a polymer (e.g., Pebax) may be heated and melted into the metal braid or mesh 70 so as to create a solid structure atop reduced diameter shaft portion 15. This polymer can provide a lower friction surface than the metal braid or mesh 70 alone, and can provide some torque transmission as well.

Figure 14:
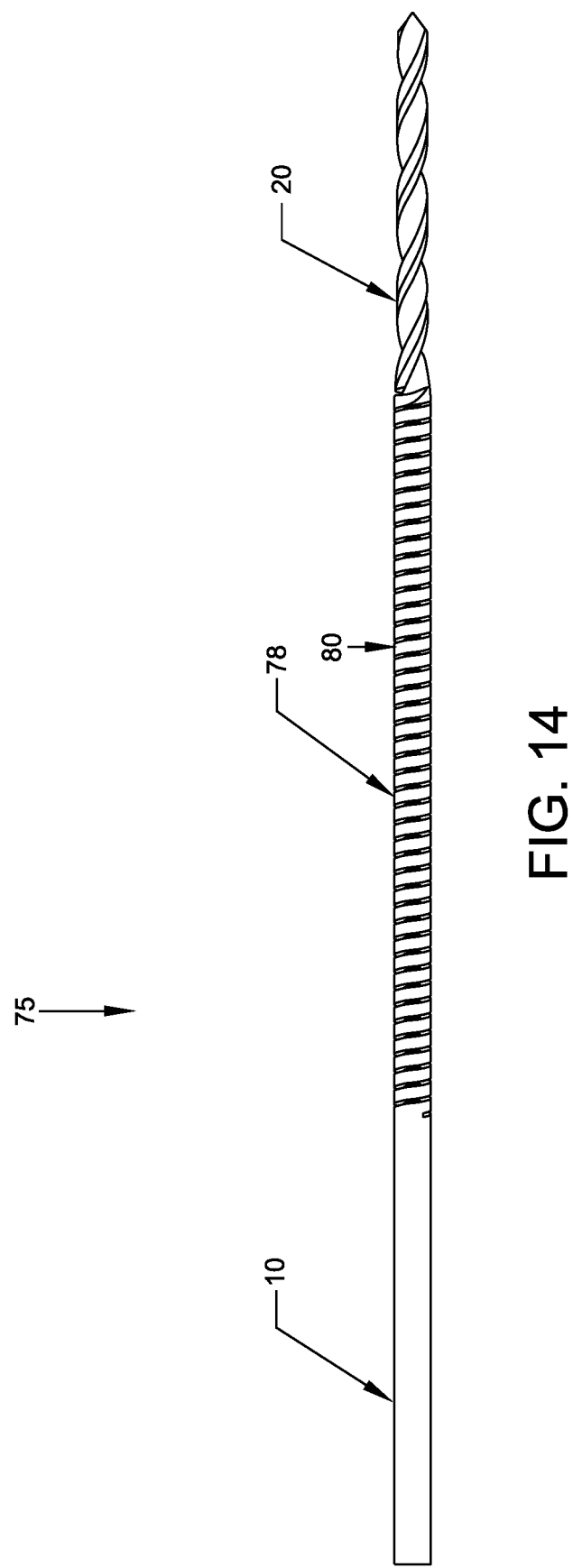
FIG. 14 is a schematic view showing another form of flexible drill bit formed in accordance with the present invention.
Figure 29:
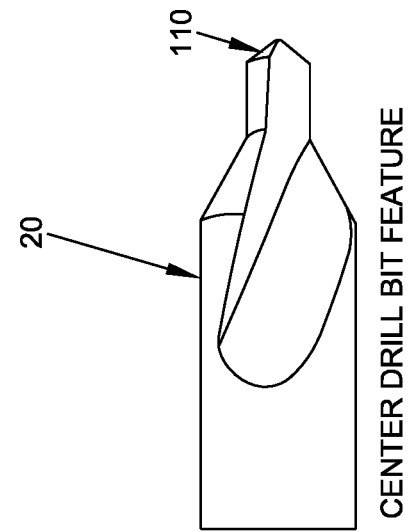
FIGS. 28-32 are schematic views showing various forms of cutting tips which may be used with the flexible drill bit of the present invention.
Figure 28:
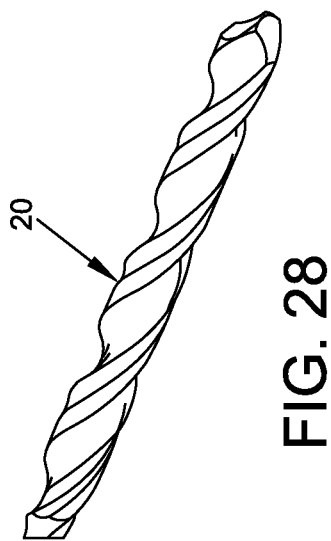
Figure 30:
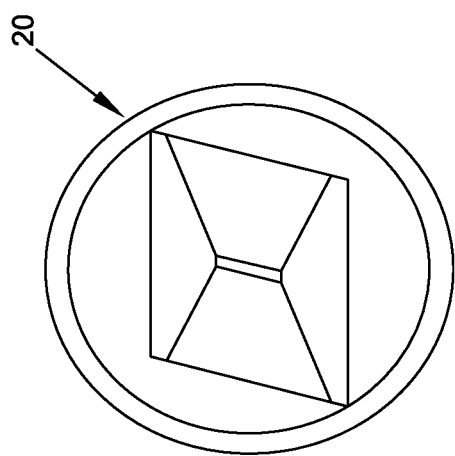
Figure 31:
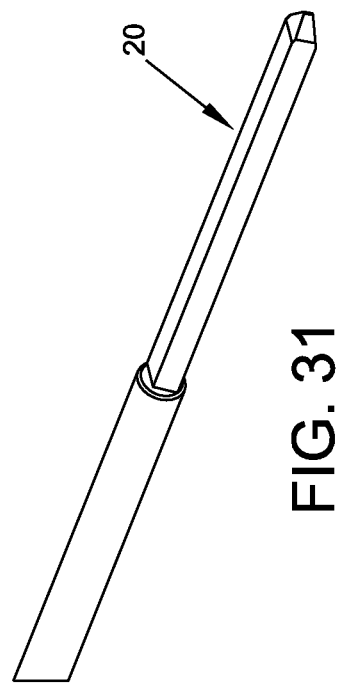

Looking next at FIG. 14, there is shown a flexible drill bit 75 which is similar to the flexible drill bit 5 shown in FIG. 1, however, instead of providing a reduced diameter shaft portion (e.g., the aforementioned reduced diameter shaft portion 15) between the full diameter shaft portion (e.g., the aforementioned full diameter shaft portion 10) and the fluted cutting tip portion (e.g., the aforementioned fluted cutting tip portion 20) in order to create the desired flexibility in the drill bit, the full diameter shaft portion extends all the way to the fluted cutting tip portion and portions of material are removed from the full diameter shaft portion so as to create the desired flexibility in the drill bit while providing greater torque carrying strength as compared to simply a reduced diameter shaft portion 15.

More particularly, in this embodiment, and looking now at FIG. 14, flexible drill bit 75 comprises a full diameter shaft portion 10 and a fluted cutting tip portion 20, with full diameter shaft portion 10 and fluted cutting tip portion 20 being formed integral with one another (i.e., a "unibody" design). In order to render the distal end 78 of full diameter shaft portion 10 flexible, material is removed from the full diameter shaft portion so as to create a flexible portion along the full diameter shaft portion of the drill bit. The material is removed in a pattern which enhances shaft flexibility but minimizes the reduction of torque transmission. In one preferred form of the invention, the material is removed in a spiral pattern as shown at 80 in FIG. 14 and may be accomplished by laser cutting, electrical discharge machining (i.e., EDM), machining, grinding or other means. For a clockwise rotating flexible drill bit 5, spiral cuts 80 are preferably formed in a clockwise pattern (when viewed from proximal to distal direction), but may also be formed in a counter-clockwise pattern.

Material may also be removed from full diameter shaft portion 10 in other patterns so as to create a flexible, yet high torque transmitting, portion along the shaft of the drill bit. By way of example but not limitation, and looking now at FIG. 15, a series of transverse slots 85 (instead of the spiral cuts 80 shown in FIG. 14) may be cut into the shaft, with the slots preferably following a spiral or other geometric pattern. Transverse slots 85 may be formed with various configurations. FIGS. 16-19 show one way of configuring transverse slots 85. FIGS. 20-23 show another way of configuring transverse slots 85. Still other ways of configuring transverse slots 85 will be apparent to those skilled in the art in view of the present disclosure.

In this embodiment if the invention, flexible drill bit 75 may comprise a material such as stainless steel or Nitinol.

Flexible Drill Bit Having a Multi-Body Construction

In another embodiment of the present invention, portions of the flexible drill bit (e.g., the cutting tip) may comprise separate components which are connected to the remaining portions of the flexible drill bit (e.g., the solid shaft) in order to provide a flexible drill bit having a multi-body construction.

More particularly, and looking now at FIGS. 24 and 25, there is a shown a flexible drill bit 90 comprising two components (i.e., full diameter shaft portion 10 and fluted cutting tip portion 20) which are connected together so as to form a flexible drill bit having three sections, i.e., a distal cutting tip, a proximal shaft and an intermediate flexible region. In this embodiment of the invention, fluted cutting tip portion 20 comprises an elongated solid shaft 95 which is received within a lumen 100 formed in full diameter shaft portion 10 and then secured therein (e.g., by welding, adhesive bond, swaging, etc. or a combination thereof or other means well known in the art). Full diameter shaft portion 10 is preferably secured to fluted cutting tip portion 20 at the distal end of full diameter shaft portion 10, e.g., at 102. Flexible drill bit 90 may comprise additional points of securement between full diameter shaft portion 10 and fluted cutting tip portion 20 (e.g., proximal of the intermediate flexible region, such as at 103). The drill bit is rendered flexible by removing material from full diameter shaft portion 10, e.g., such as by forming spiral cuts 80 in full diameter shaft portion 10. Although spiral cuts 80 are shown in FIGS. 24 and 25 as being formed in a clockwise pattern (when viewed from proximal to distal direction), they preferably would be formed in a counter-clockwise pattern when used with a clockwise-rotating drill (when viewed from proximal to distal) so that the spiral cuts would tend to tighten down on the elongated solid shaft 95 during drilling. Alternatively, and looking now at FIGS. 26 and 27, the material may be removed as an interrupted spiral cut 105 so as to provide the desired flexibility to the drill bit. In one preferred form of this embodiment, the cuts are interrupted segment lengths of less an 120 degrees around the perimeter, have a opening—or width—which is less than the pitch distance (i.e., longitudinal distance between adjacent cuts), and have a gap between laser cuts which is approximately equal to the pitch distance. In one preferred form of this embodiment, the cuts have a slight angle relative to perpendicular to the longitudinal axis of the flexible drill bit 90.

Depending on the location(s) of securement between full diameter shaft portion 10 and fluted cutting tip portion 20 (e.g., at securement point 102, securement point 103, etc.), the torque may be transmitted through the full diameter shaft portion 10 (distal securement only), through solid shaft 95 of fluted cutting tip portion 20 (proximal securement only) or shared between the two (both the proximal and distal securements).

Cutting Tip Constructions

Figure 32:
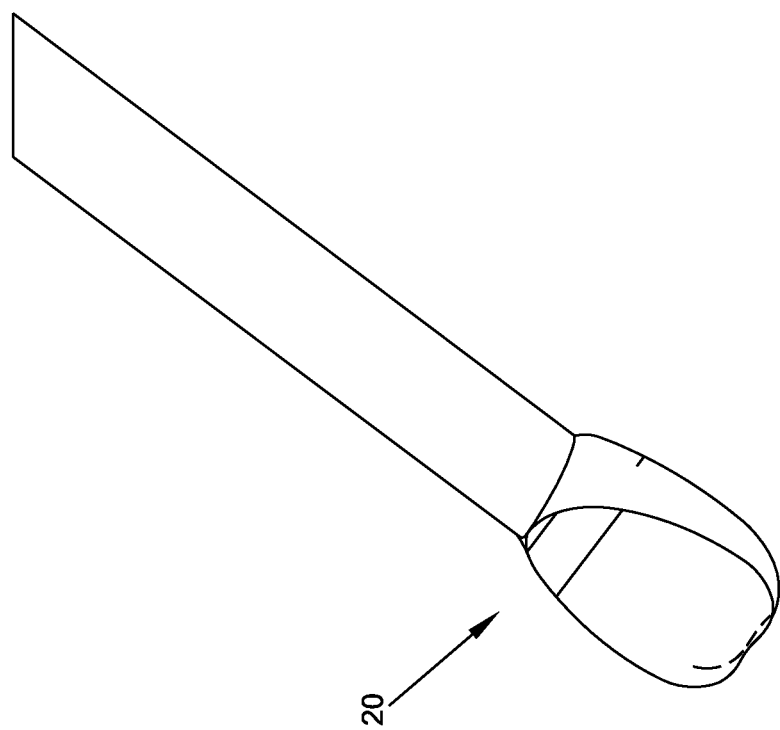

Looking now at FIGS. 28-32, there are shown various shapes and designs of cutting tips which may be used in accordance with the present invention, e.g., a fluted cutting tip (FIG. 28), a fluted cutting tip with a centering feature 110 similar to a center drill bit (FIG. 29), a diamond shape (FIGS. 30 and 31) or a forged or flattened tip (FIG. 32). In the cutting tip embodiment of a fluted cutting tip (e.g., FIG. 28), the inclusive angle at the tip may be approximately 30-120 degrees, is more preferably approximately 60-90 degrees, and is most preferably approximately 70 degrees.

Helical Structures

In the foregoing disclosure, various constructions are provided in which the flexible drill bit comprises a helical structure. By way of example but not limitation, a helical coil 60 is mounted over reduced diameter shaft portion 15 (FIGS. 10 and 11), a helical groove is formed in full diameter shaft portion 10 (FIGS. 14 and 24-27), etc. These constructions are provided in order to maximize the flexibility of the drill bit while minimizing reduction of torque transmission through the drill bit. In this respect it will be appreciated that the configuration of the helical structure (i.e., the direction of the spiral) is preferably related to the direction of the applied torque, in order to maintain maximum torque transmission through the drill bit. However, the relationship of these may vary depending on the specific construction of the drill bit.

In the embodiment of a helical coil mounted over a reduced diameter shaft portion (FIGS. 10 and 11), where the torque is intended to be applied in a clockwise direction (when viewed from the proximal end of the drill bit), it is preferred that the helix rotate counter-clockwise as it advances down the drill bit, and where the torque is intended to be applied in a counter-clockwise direction (when viewed from the proximal end of the drill bit), it is preferred that the helix rotate clockwise as it advances down the drill bit. Such an inverse relationship between the direction of the applied torque and the direction of the spiral will ensure that any deformation of the helical coil from the applied torque will cause the helical coil to tighten, whereby to preserve torque transmission through the helical coil.

In the embodiment of a helical groove formed in a full diameter shaft portion (FIGS. 14 and 24-27), where the torque is intended to be applied in a clockwise direction (when viewed from the proximal end of the drill bit), it is preferred that the helix rotate counter-clockwise as it advances down the drill bit, and where the torque is intended to be applied in a counter-clockwise direction (when viewed from the proximal end of the drill bit), it is preferred that the helix rotate clockwise as it advances down the drill bit. The appropriate relationship between the direction of the applied torque and the direction of the spiral will maximize torque transmission while maintaining drill bit flexibility.

General Construction

The flexible drill bit may comprise Nitinol or stainless steel or any other material which is flexible enough to bend into a curved state, and strong enough to transmit the torsional forces required for drilling into bone.

The entire shaft or portions of the shaft can be coated to reduce friction (e.g., with curved drill guide 35 and/or bone 40).

Angled Drill Guide For Use With Flexible Drill Bit

In the preceding description, a flexible drill bit is disclosed for use in drilling a hole in material (e.g., bone) where the angle of approach is offset from the angle at which the drill is to enter the material.

In accordance with the present invention, there is now also provided a novel angled drill guide which may be used to guide entry of the flexible drill bit into the target material (e.g., bone) while the flexible drill bit is in its curved configuration.

Figure 33:
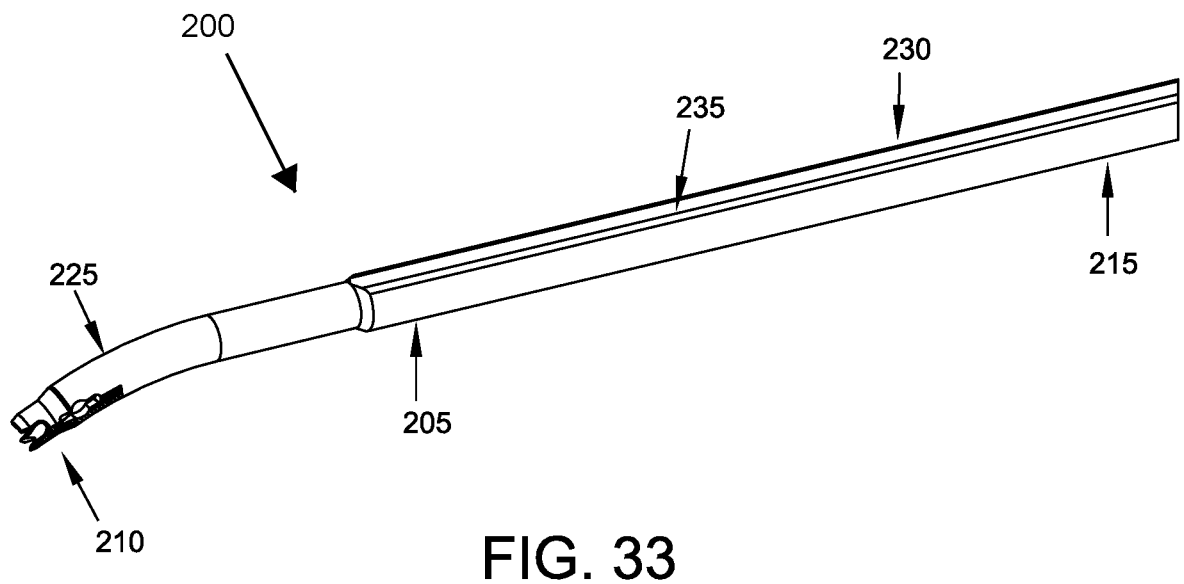
FIGS. 33-36 are schematic views showing a novel angled drill guide formed in accordance with the present invention.
Figure 34:
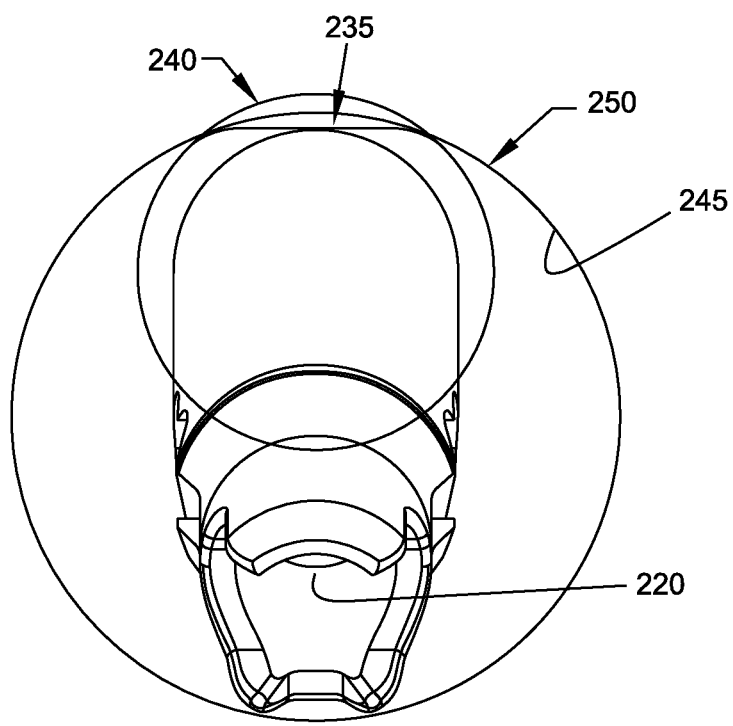

More particularly, and looking now at FIGS. 33 and 34, in one preferred form of the invention, there is provided a novel angled drill guide 200 for use in guiding a flexible drill bit (e.g., such as a flexible drill bit discussed above) into target material (e.g., bone). Novel angled drill guide 200 generally comprises an elongated shaft 205 having a distal end 210, a proximal end 215 and a lumen 220 extending therebetween. Preferably elongated shaft 205 has a curved distal portion 225 and a straight proximal portion 230.

In order to allow angled drill guide 200 to be formed with a greater degree of curvature and still pass through the interior lumen of a straight access cannula, at least a portion of straight proximal portion 230 (and, optionally, a portion of curved distal portion 225) is formed with a flat 235 extending therealong, with flat 235 being formed on the same side as the outside of the curve. Flat 235 reduces the effective diameter of elongated shaft 205 so as to minimize interference between the angled drill guide and the side wall of the straight access cannula, thereby allowing angled drill guide 200 to be formed with a greater degree of curvature while still fitting through the straight access cannula with a preferred diameter (e.g., 8 mm inner diameter). See, for example, FIG. 34, which shows how flat 235 on elongated shaft 205 eliminates the area of interference 240 created between angled drill guide 200 and the side wall 245 of a straight access cannula 250.

It will be appreciated that the provision of the flat 235 on elongated shaft 205 can also be used with a curved access cannula so as to eliminate an area of interference between an angled drill guide and the curved access cannula, e.g., where the angled drill guide has an angle of curvature which is greater than the angle of curvature of the curved access cannula.

Figure 35:
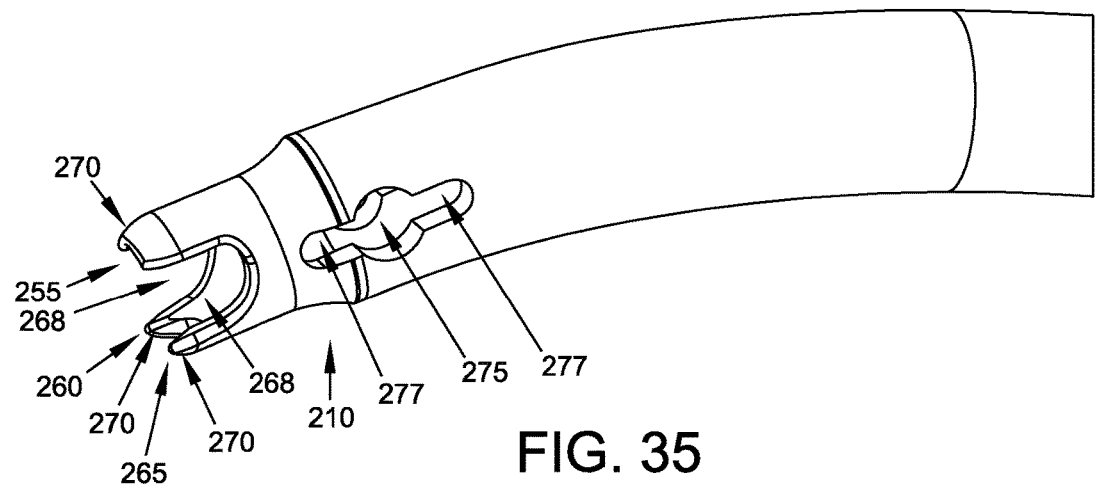
Figure 36:
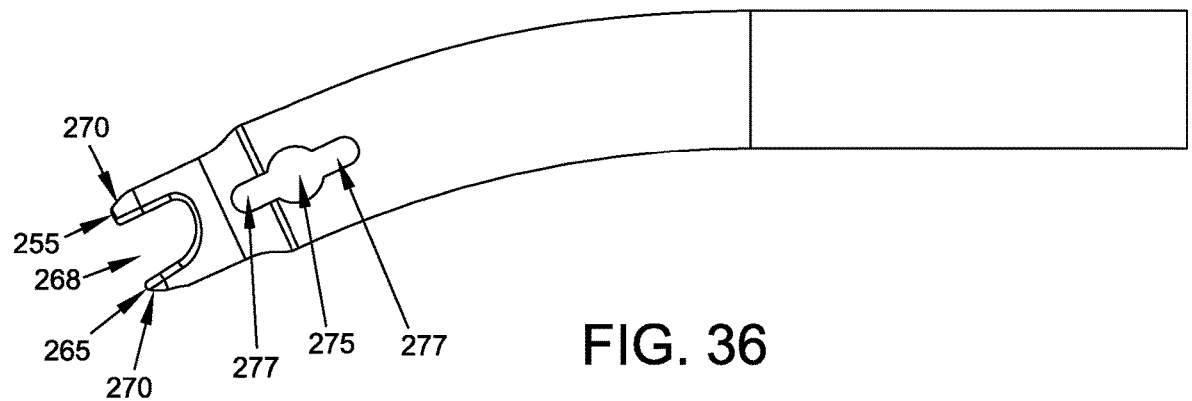

Looking now at FIGS. 35 and 36, it will be seen that the distal end 210 of elongated shaft 205 may be formed with three teeth 255, 260, 265 for engaging the surface of the material (e.g., bone) which is to be drilled. Tooth 255 serves to provide a stable support against the material (e.g., bone) which is to be drilled. To this end, tooth 255 is relatively large and is set at the outer perimeter of the curve of angled drill guide 200, thus providing a smooth, continuous surface for a flexible drill bit to ride against as the flexible drill bit passes out the distal end of angled drill guide 200. Specifically, the flexible drill bit may have a tendency to follow the outer perimeter of the curve of angled drill guide 200 when the flexible drill bit is in a flexed state. The cutting edges of the flexible drill bit may catch and/or bear against any irregularities in the surface of angled drill guide 200; therefore, it is preferable to maintain a smooth, uninterrupted surface for the flexible drill bit to bear against. In one preferred form of the invention, tooth 255 extends along approximately 90-180 degrees of the perimeter of the angled drill guide, and preferably along approximately 115 degrees of the perimeter of the angled drill guide. Teeth 260, 265 serve to grip into the material (e.g., bone) which is to be drilled. This is especially significant with an angled drill guide 200, as there are forces imparted on the angled drill guide 200 while drilling into bone (and/or when thereafter implanting an anchor into bone using the angled drill guide) which can tend to make the distal end of the angled drill guide 200 skid along the material (e.g., bone). To this end, teeth 260, 265 are relatively thin and are set at the inner perimeter of the curve of angled drill guide 200. Slots 268 allow the user to view a flexible drill bit exiting the angled drill guide 200. Preferably teeth 255, 260, 265 are radiused at their distal ends (e.g., as shown at 270) so as to facilitate passage of angled drill guide 200 through an access cannula (which may be either straight or curved).

In one preferred form of the invention, angled drill guide 200 also comprises side windows 275 disposed proximal to teeth 255, 260, 265. Preferably side windows 275 have side cuts 277 extending proximally and distally from side windows 275, with side cuts 277 being aligned with the longitudinal axis of angled drill guide 200. Windows 275 allow the user to view a flexible drill bit extending though angled drill guide 200; by providing appropriate markings (not shown) along the shaft of the flexible drill bit, the user can (by aligning those drill bit markings with windows 275) tell the depth to which the flexible drill bit is drilling into the material (e.g., bone), and/or tell the depth to which a bone anchor (being inserted through angled drill guide 200) is inserted into the material (e.g., bone).

Figure 37:
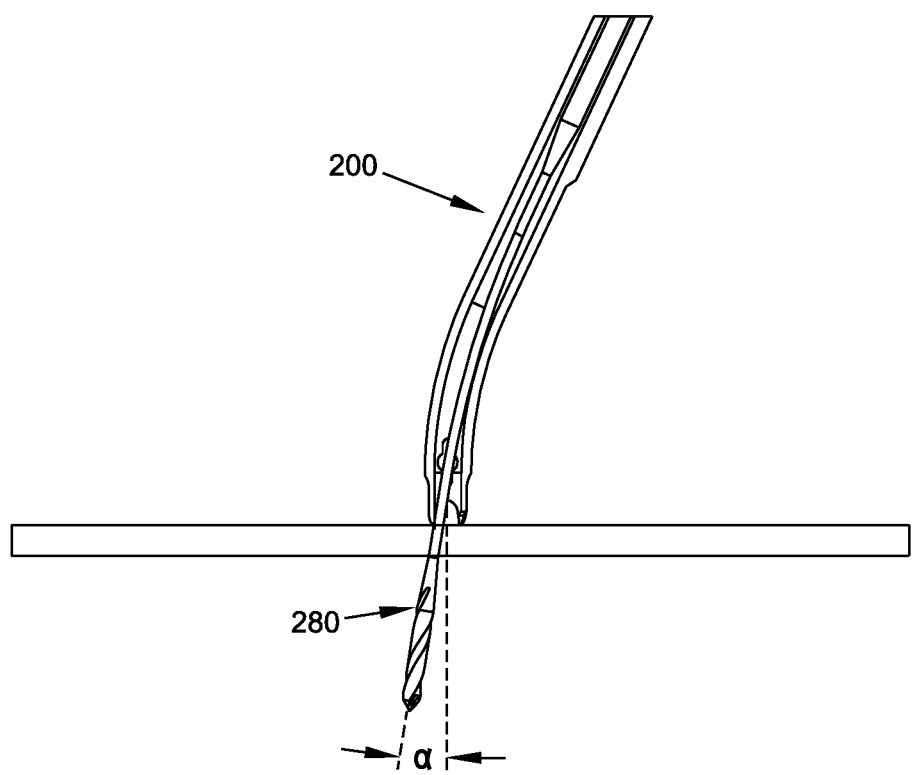
FIG. 37 is a schematic view showing how a flexible drill bit exiting the distal end of an angled drill guide will tend to exit the angled drill guide with an off-centered disposition.

Significantly, where a flexible drill bit passes through an angled drill guide having a curve, the flexible drill bit will tend to bear against the outside of the curve. As a result, when the flexible drill bit exits the distal end of an angled drill guide, the flexible drill bit will tend to exit the distal end of the angled drill guide 200 with an off-angle disposition. See FIG. 37, where a flexible drill bit 280 is shown exiting angled drill guide 200 with offset angle α.

Figure 38:
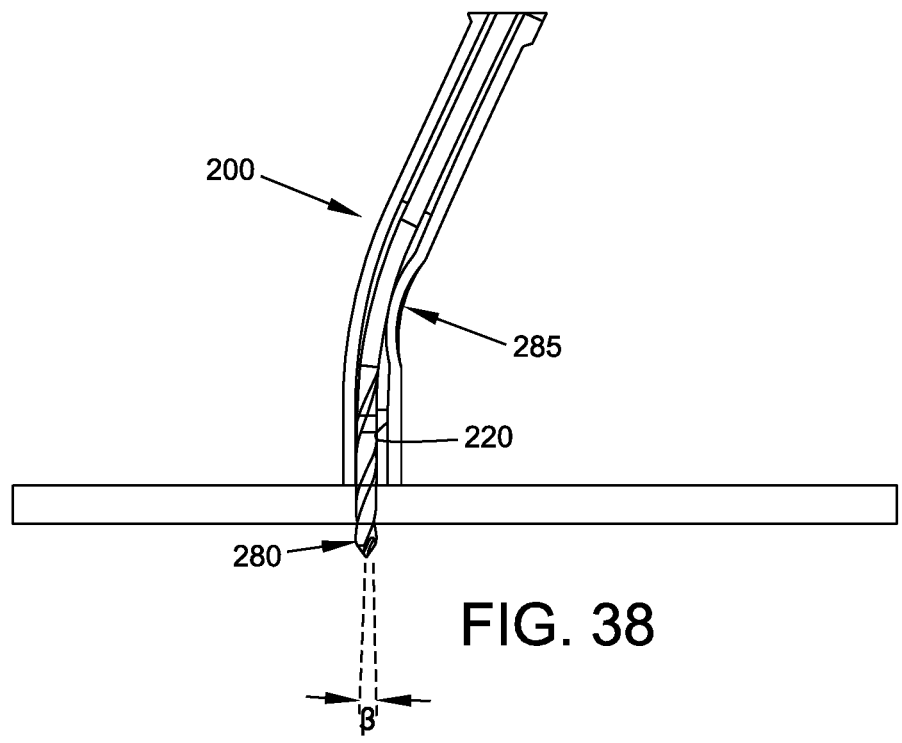
FIG. 38 is a schematic view showing how an angled drill guide may be provided with a dimple so as to re-center the flexible drill bit as it exits the distal end of the angled drill guide.

To counteract this effect, and looking now at FIG. 38, angled drill guide 200 may be provided with a dimple 285 in the side wall of the angled drill guide. Dimple 285 is diametrically-opposed to the outside of the curve of angled drill guide 200, and effectively narrows lumen 220. As a result of this construction, when a flexible drill bit is disposed in lumen 220 of the angled drill guide, dimple 285 forces the flexible drill bit into a smaller bend radius that more closely matches the bend radius of the angled drill guide, whereby to re-align the flexible drill bit as it exits the distal end of the angled drill guide 200 and create offset angle β (offset angle β is less than the aforementioned offset angle α). This can be particularly beneficial if the flexible drill bit has a reduced diameter along the length which passes through the curved portion of the angled drill guide 200 (e.g., proximal to the cutting portion as discussed above).

Figure 39:
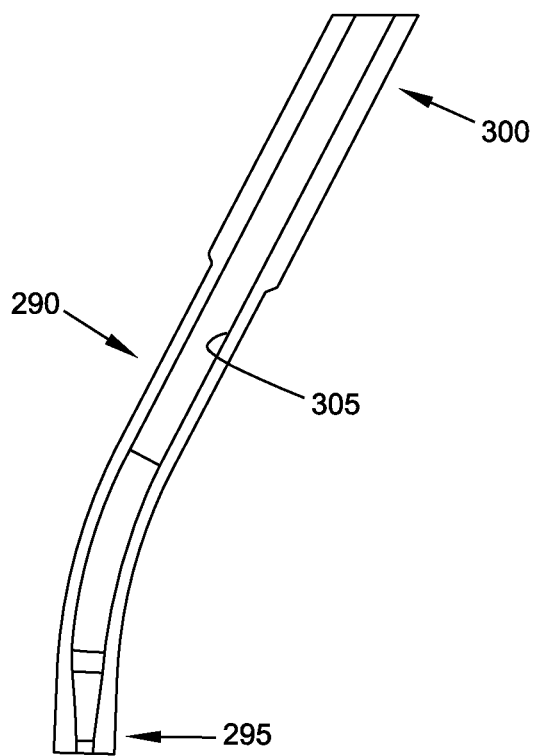
FIGS. 39 and 40 are schematic views showing how an angled drill guide may be provided with a tapered inner lumen so as to re-center the flexible drill bit as it exits the distal end of the angled drill guide.

FIG. 39 shows another approach for centering and aligning the flexible drill bit as it exits the distal end of the angled drill guide 290. More particularly, FIG. 39 shows an angled drill guide 290 having a distal end 295, a proximal end 300 and a lumen 305 extending therebetween. In this form of the invention, lumen 305 tapers inwardly (i.e., narrows) at the distal end of angled drill guide 290, whereby to constrain the orientation of a flexible drill bit to a re-centered and re-aligned disposition as it exits the distal end of the angled drill guide. In one preferred form of the invention, lumen 305 narrows so as to provide a bearing structure having a relatively close sliding fit with a flexible drill bit disposed in the angled drill guide, whereby to provide good support for the flexible drill bit as it emerges from the distal end of the angled drill guide. Thus, the flexible drill bit will be more centered with the center axis of the angled drill guide, and will be more angularly aligned with the curvature at the distal end of the angled drill guide.

Figure 40:
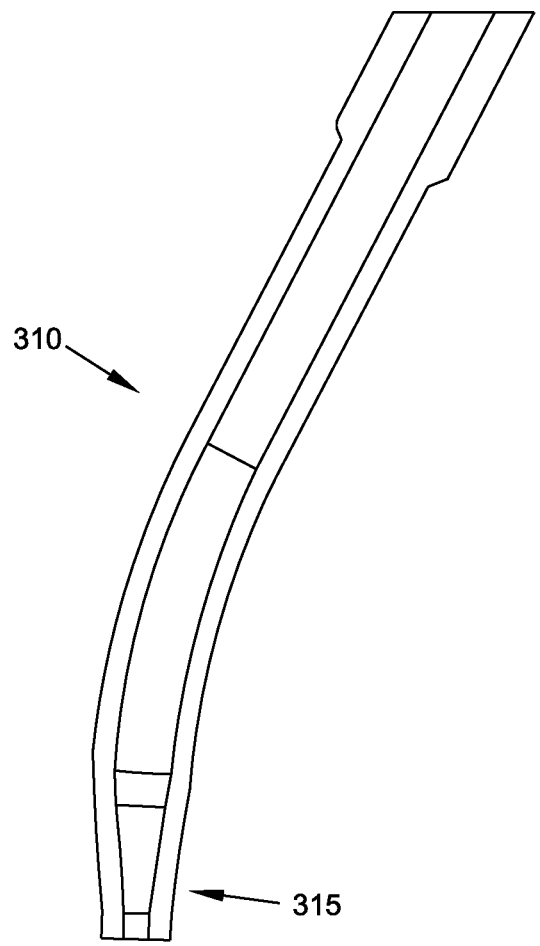

FIG. 40 shows another angled drill guide 310. Angled drill guide 310 is substantially identical to the angled drill guide 290 shown in FIG. 39, except that with the angled drill guide 310 shown in FIG. 40, distal end 315 of angled drill guide 310 has a tapered outer diameter (as well as a tapered inner diameter) so as to facilitate disposition of the angled drill guide about a drilling site.

Figure 41:
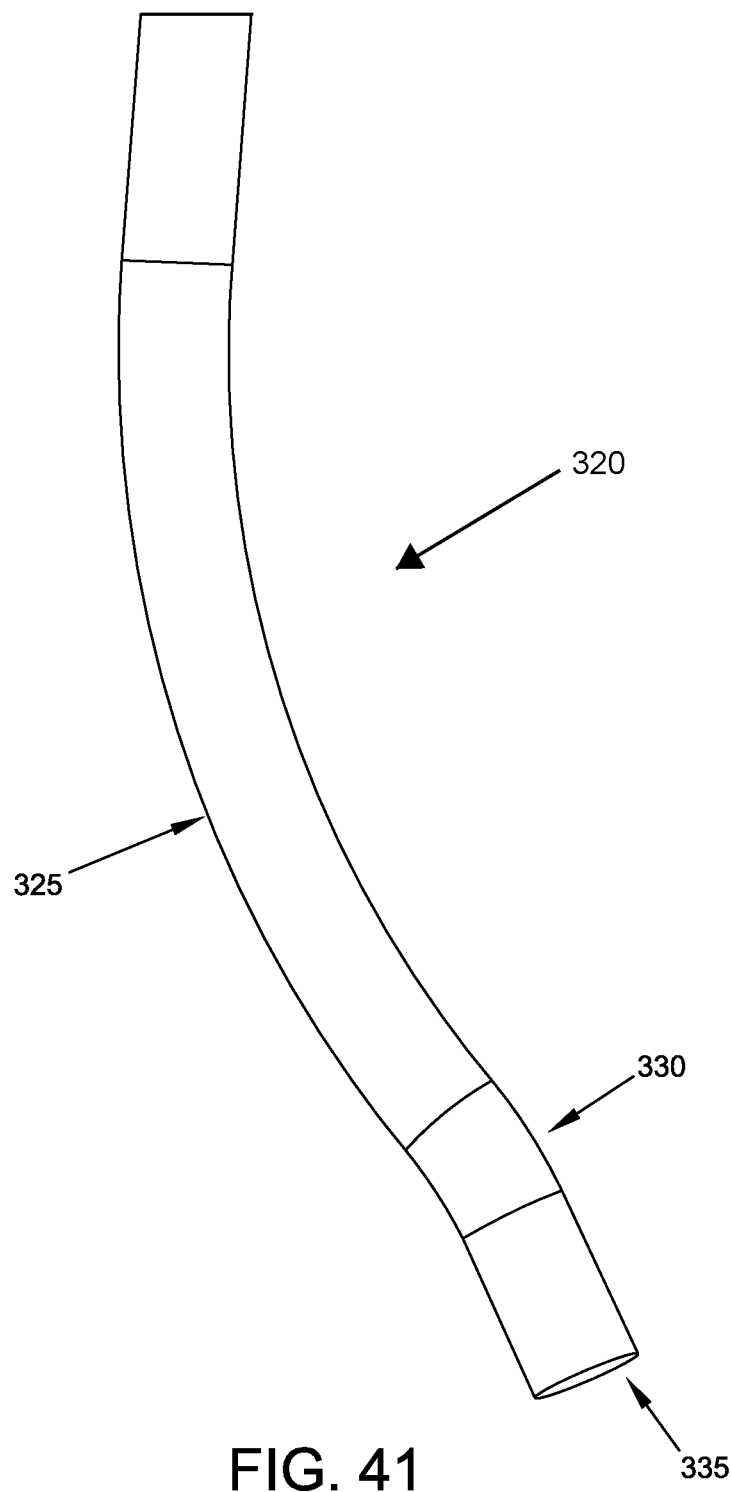
FIG. 41 is a schematic view showing how an angled drill guide may be provided with compound curves so as to re-center the flexible drill bit as it exits the distal end of the angled drill guide.

In another form of the present invention, and looking now at FIG. 41, there is shown an angled drill guide 320 which uses the combination of two curves 325, 330 to help center and align the flexible drill bit as it emerges from the distal end 335 of the angled drill guide. More particularly, as noted above, where a flexible drill bit passes through an angled drill guide having a curve, the flexible drill bit will tend to follow the outside of the curve. As a result, when the flexible drill bit exits the distal end of an angled drill guide, the flexible drill bit will tend to exit the distal end of the angled drill guide with an off-centered and mis-aligned disposition. To counteract this effect, the angled drill guide 320 shown in FIG. 41 is formed with two curves 325, 330—the curve 325 is the primary curve of the angled drill guide, providing the curvature needed for the flexible drill bit to access the drilling site, and the curve 330 is the secondary curve of the angled drill guide, providing the "remedial" curvature used to re-center and re-align the flexible drill bit as it exits the distal end 335 of angled drill guide 320.

Figure 42:
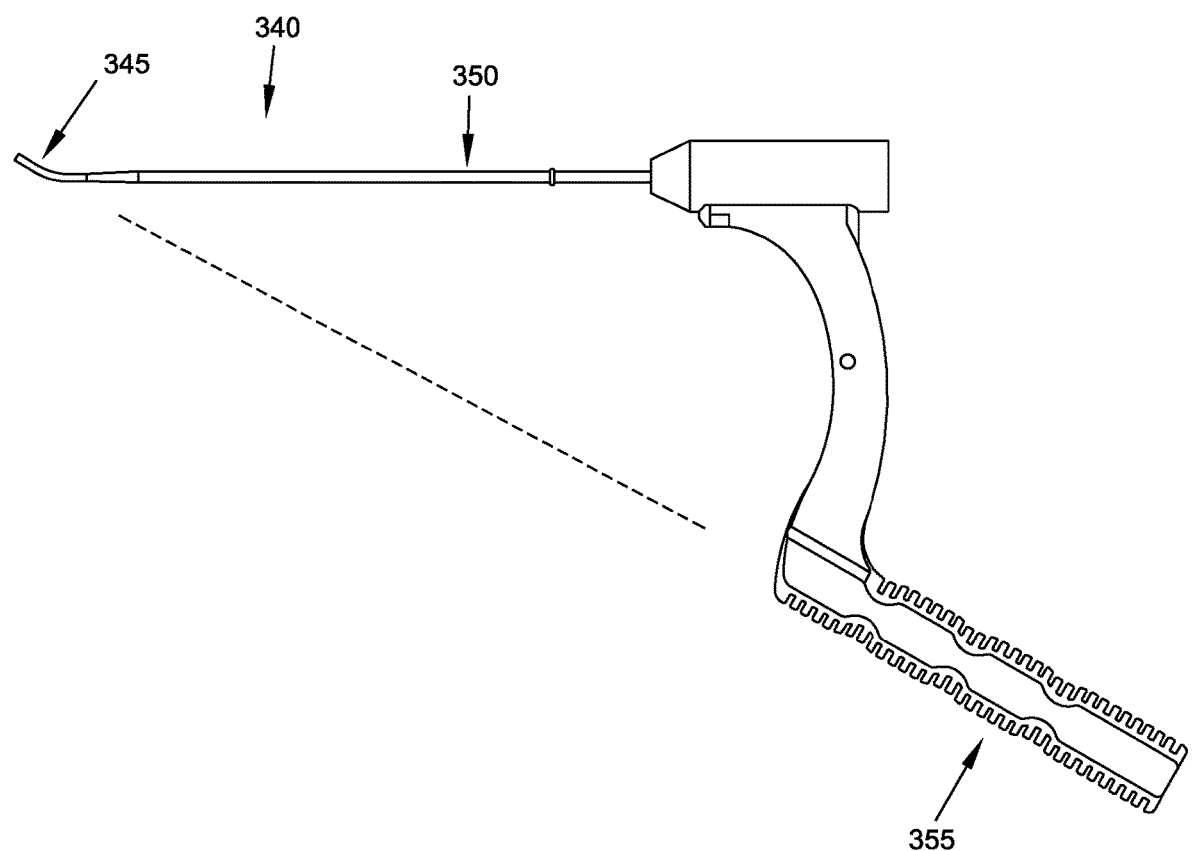
FIG. 42 is a schematic view showing how an angled drill guide may be provided with a novel handle so as to facilitate pushing the distal end of the angled drill guide directly against the outer surface of the material (e.g., bone) which is to be drilled, whereby to provide more stable drilling.

In another form of the present invention, and looking now at FIG. 42, an angled drill guide 340 having a curved distal section 345 and a straight proximal section 350 may be provided with a handle 355 which is offset from the longitudinal axis of the proximal section 350 of the angled drill guide, but which is aligned with the distal section 345 of the angled drill guide, so as to allow the user to better hold the angled drill guide against the material (e.g., bone) which is to be drilled. In essence, by aligning the longitudinal axis of handle 355 with the longitudinal axis of the distal section 345 of the angled drill guide, the user can push the distal end of the angled drill guide directly against the surface of the material (e.g., bone) which is to be drilled, thereby providing more stability during drilling. In other words, the tip of the angled drill guide will be better engaged with the bone and hence less likely to skid along the bone while the hole is being drilled with the angled drill guide and/or an anchor is being placed into the bone hole through the angled drill guide. This is significant, since the forces created during drilling and/or anchor placement through an angled drill guide have a tendency to move the distal end of the angled drill guide relative to the material (e.g., bone) which is being drilled.

It is also possible to make an articulating angled drill guide.

Figures 43, 44:
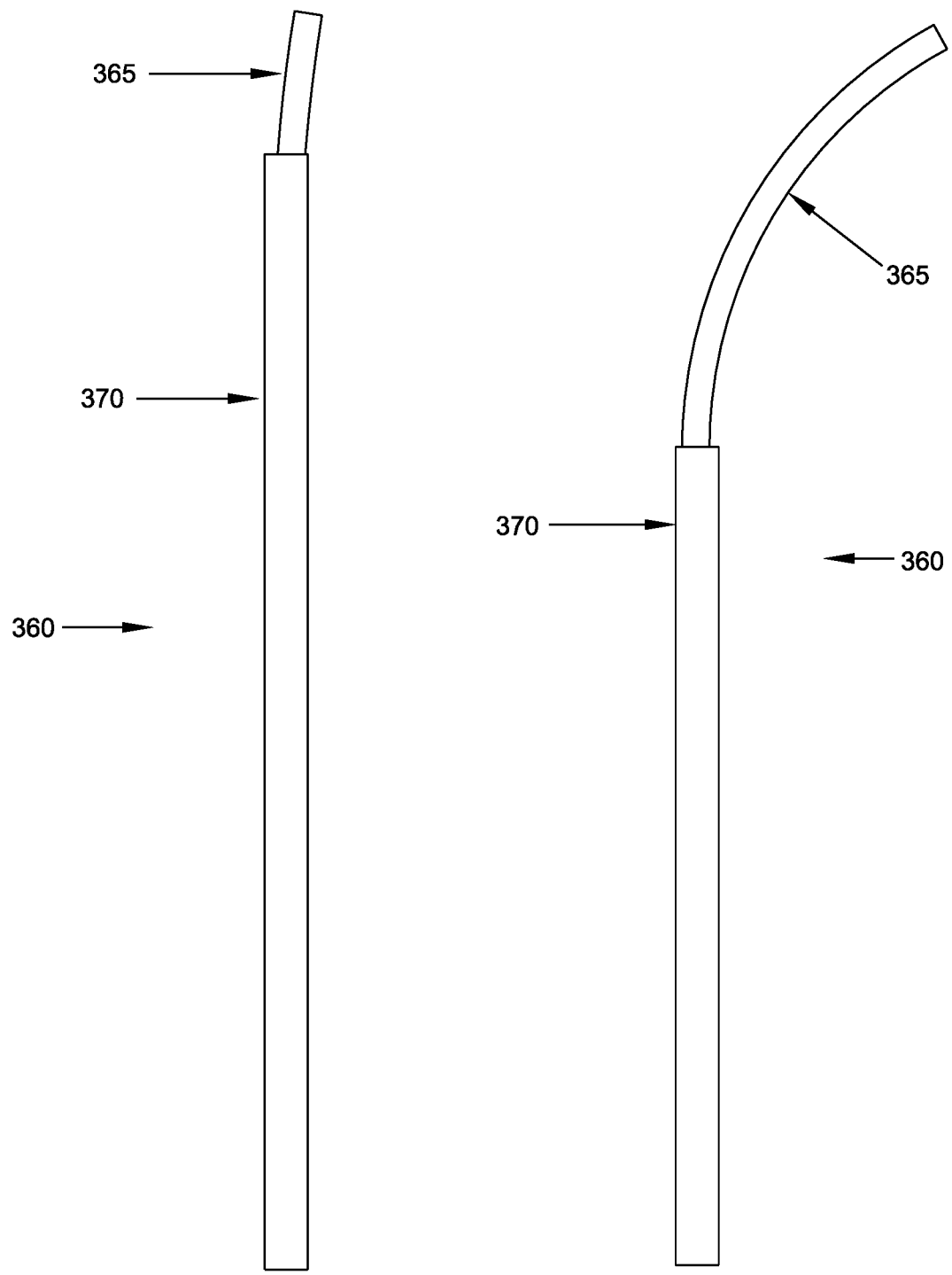
FIGS. 43 and 44 are schematic views showing a novel articulating angled drill guide formed in accordance with the present invention.

Thus, for example, and looking now at FIGS. 43 and 44, an angled drill guide 360 may comprise a curved inner sheath 365 for receiving a flexible drill bit (not shown), and a straight outer sheath 370 for overlying some or all of curved inner sheath 365. In this form of the invention, curved inner sheath 365 is in telescoping relation to straight outer sheath 370: retracting curved inner sheath 365 into straight outer sheath 370 causes the curved inner sheath 365 to straighten, while extending curved inner sheath 365 out of straight outer sheath 370 allows the curved inner sheath 365 to curve. Thus, by controlling the disposition of curved inner sheath 365 vis-à-vis straight outer sheath 370, the degree of curvature of the curved inner sheath 365 (and hence the degree of curvature of the angled drill guide as a whole) can be controlled. Curved inner sheath 365 and straight outer sheath 370 are preferably constructed of biocompatible metals; more preferably, curved inner sheath 365 is constructed of superelastic Nitinol and straight outer sheath 370 is constructed of stainless steel.

Figure 45:
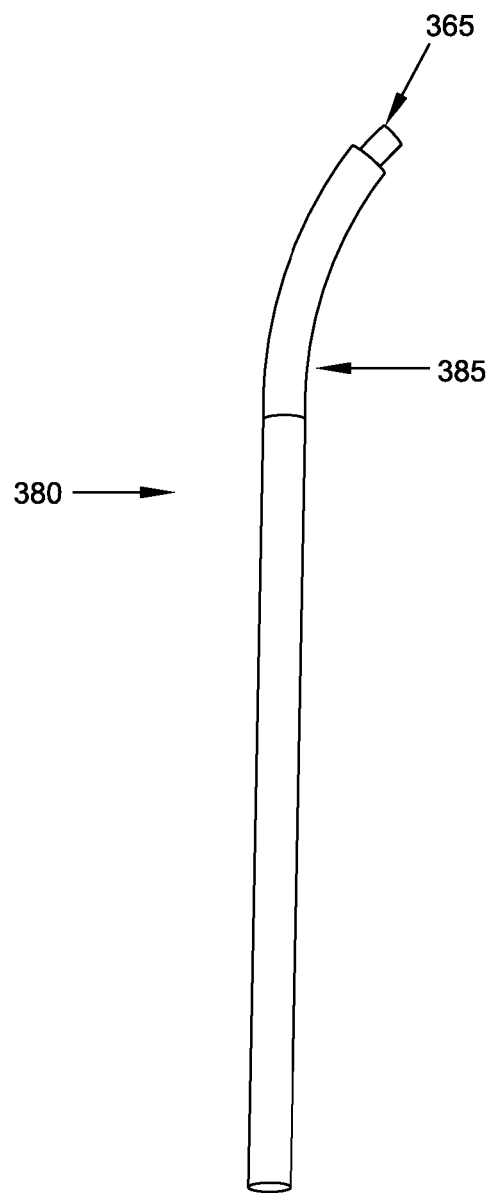
FIGS. 45 and 46 are schematic views showing another novel articulating angled drill guide formed in accordance with the present invention.
Figure 46:
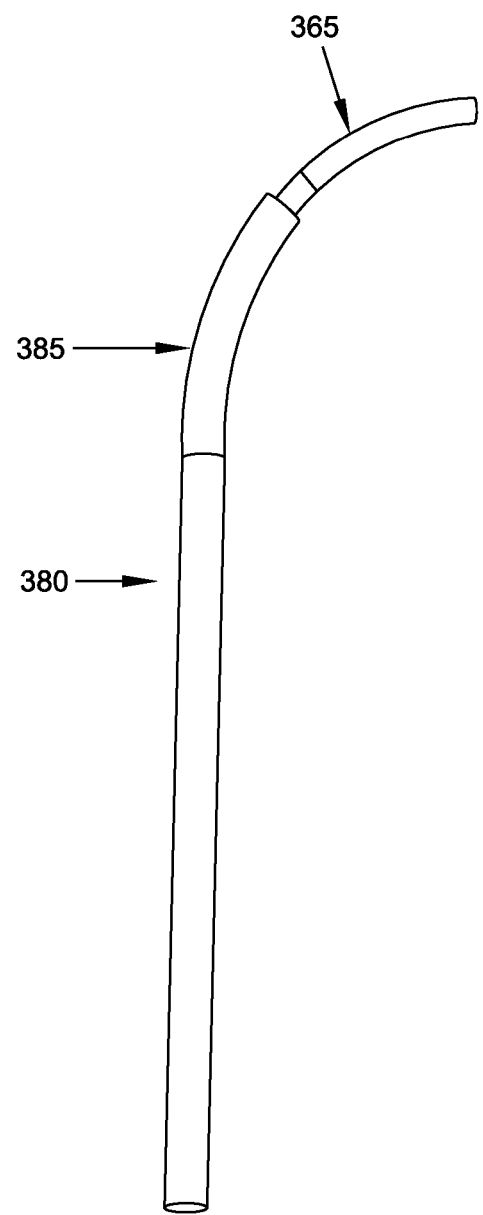

FIGS. 45 and 46 show another articulating drill guide 380. More particularly, articulating drill guide 380 is identical to the articulating drill guide 360 shown in FIGS. 43 and 44, except that curved inner sheath 365 is slidably disposed in a curved outer sheath 385, wherein curved outer sheath 385 has a lesser degree of curvature than curved inner sheath 365. Again, by controlling the disposition of curved inner sheath 365 vis-à-vis curved outer sheath 370, the degree of curvature of the curved inner sheath 365 (and hence the degree of curvature of the angled drill guide as a whole) can be controlled. Curved inner sheath 365 and curved outer sheath 385 are preferably constructed of biocompatible metal; more preferably, curved inner sheath 365 is constructed of superelastic Nitinol and curved outer sheath 385 is constructed of stainless steel.

Another articulating angled drill guide 390 is shown in FIGS. 47-49. Articulating angled drill guide 390 comprises a curved inner sheath 395 for receiving a flexible drill bit (not shown), and a curved outer sheath 400 for overlying most of curved inner sheath 395. In this form of the invention, rotating curved inner sheath 395 and curved outer sheath 400 relative to one another causes the curves to either (i) counteract one another, whereby to straighten the assembly (see FIG. 48), or (ii) to reinforce one another, whereby to curve the assembly (FIG. 49), or (iii) provide some disposition therebetween (FIG. 49A). Curved inner sheath 395 and curved outer sheath 400 are constructed on biocompatible metal, and preferably of superelastic Nitinol. In order for the curved inner sheath 395 and curved outer sheath 400 to counteract one another (whereby to straighten the assembly), their bending stiffnesses should be similar. However, since the curved outer sheath 400 has a larger diameter, a difference in wall thickness and/or material properties is required in order to achieve a similar bending stiffness. In one example, where both curved inner sheath 395 and curved outer sheath 400 are the same material (e.g., superelastic Nitinol), the curved outer sheath 400 needs to have a thinner wall to achieve a similar bending stiffness to the curved inner sheath 395.

Figure 50:
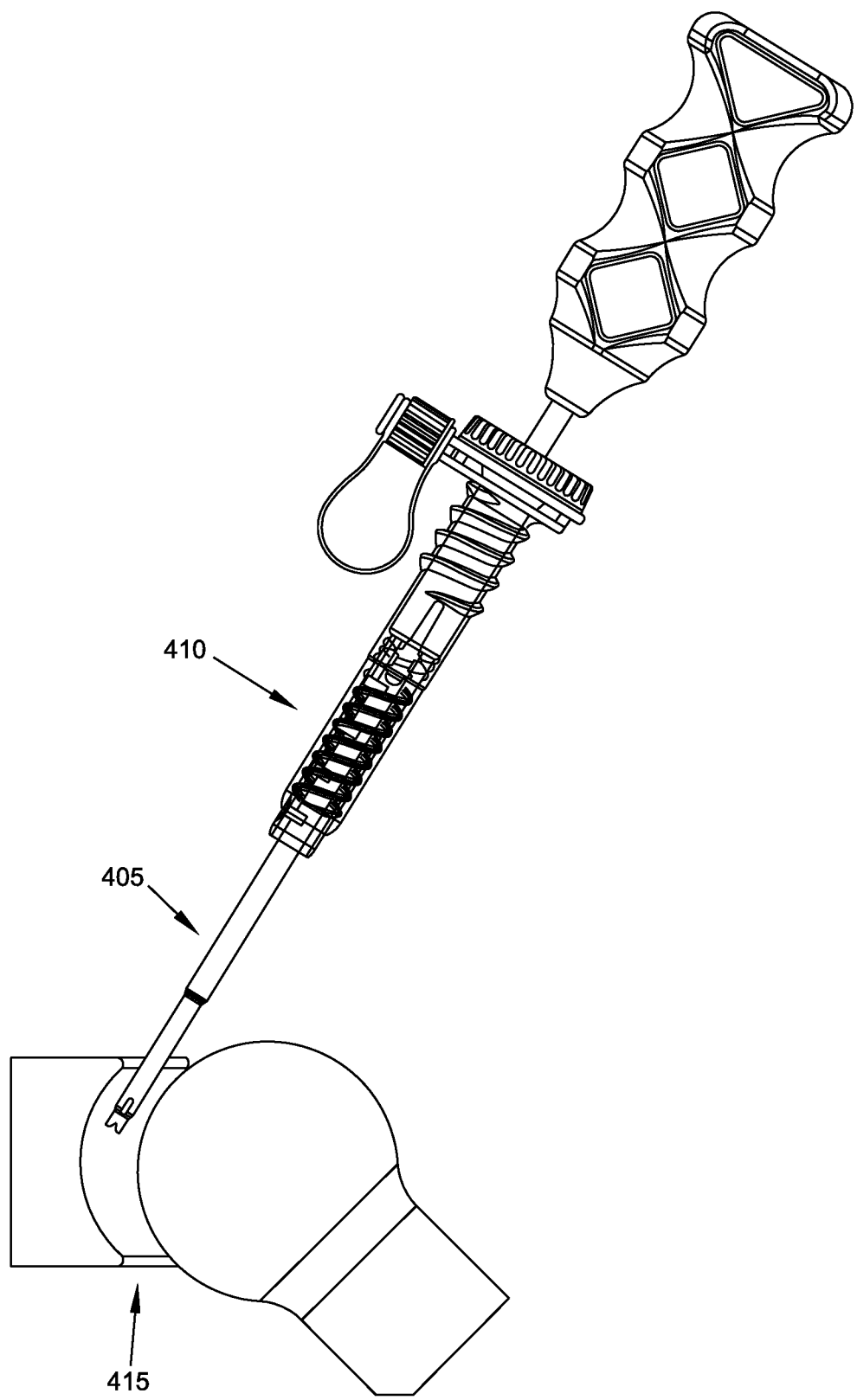
FIGS. 50-57 are schematic views showing how an articulating angled drill guide and flexible drill bit may be used to drill a hole in a surface of a joint.
Figure 51:
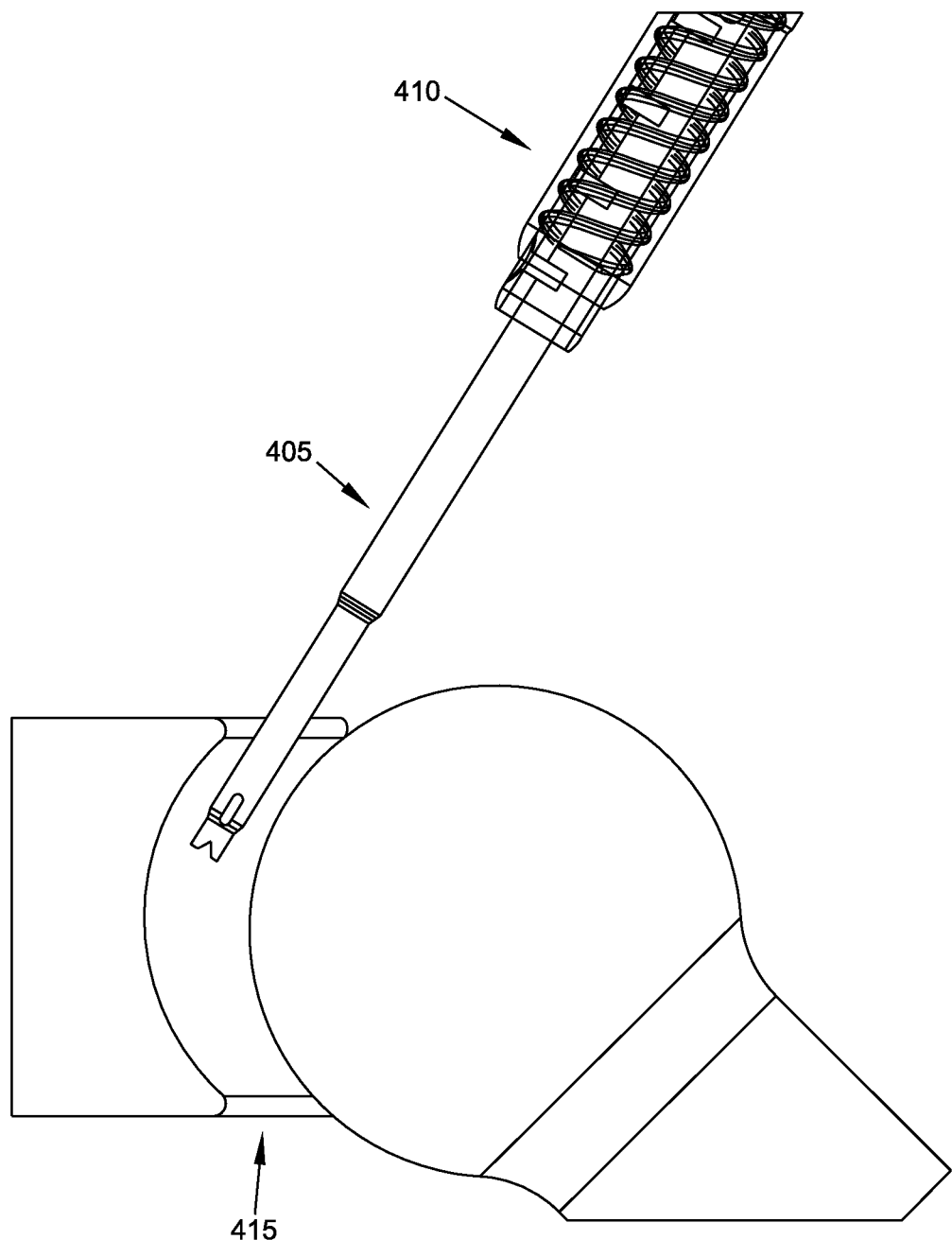
Figure 52:
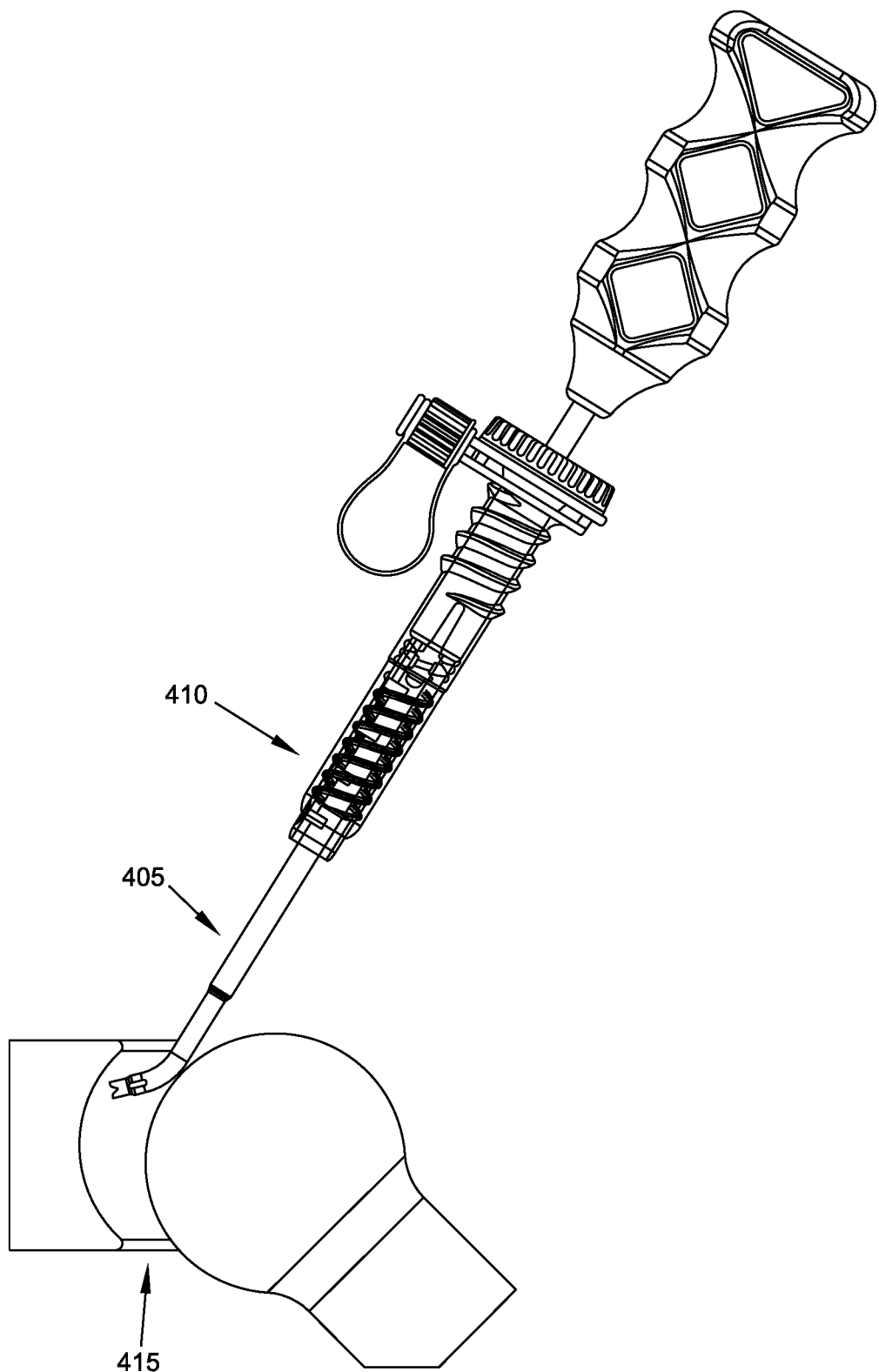
Figure 53:
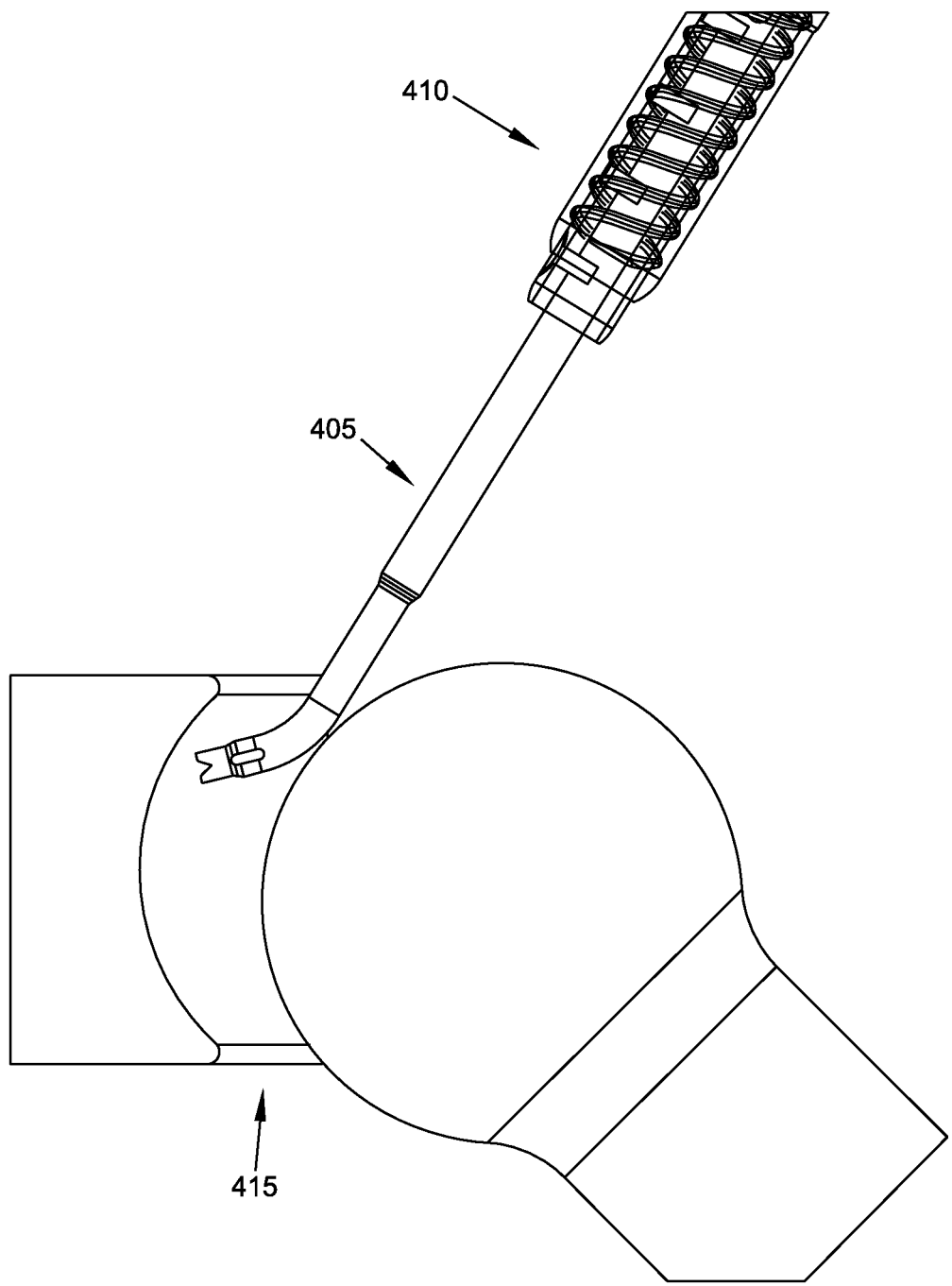
Figure 54:
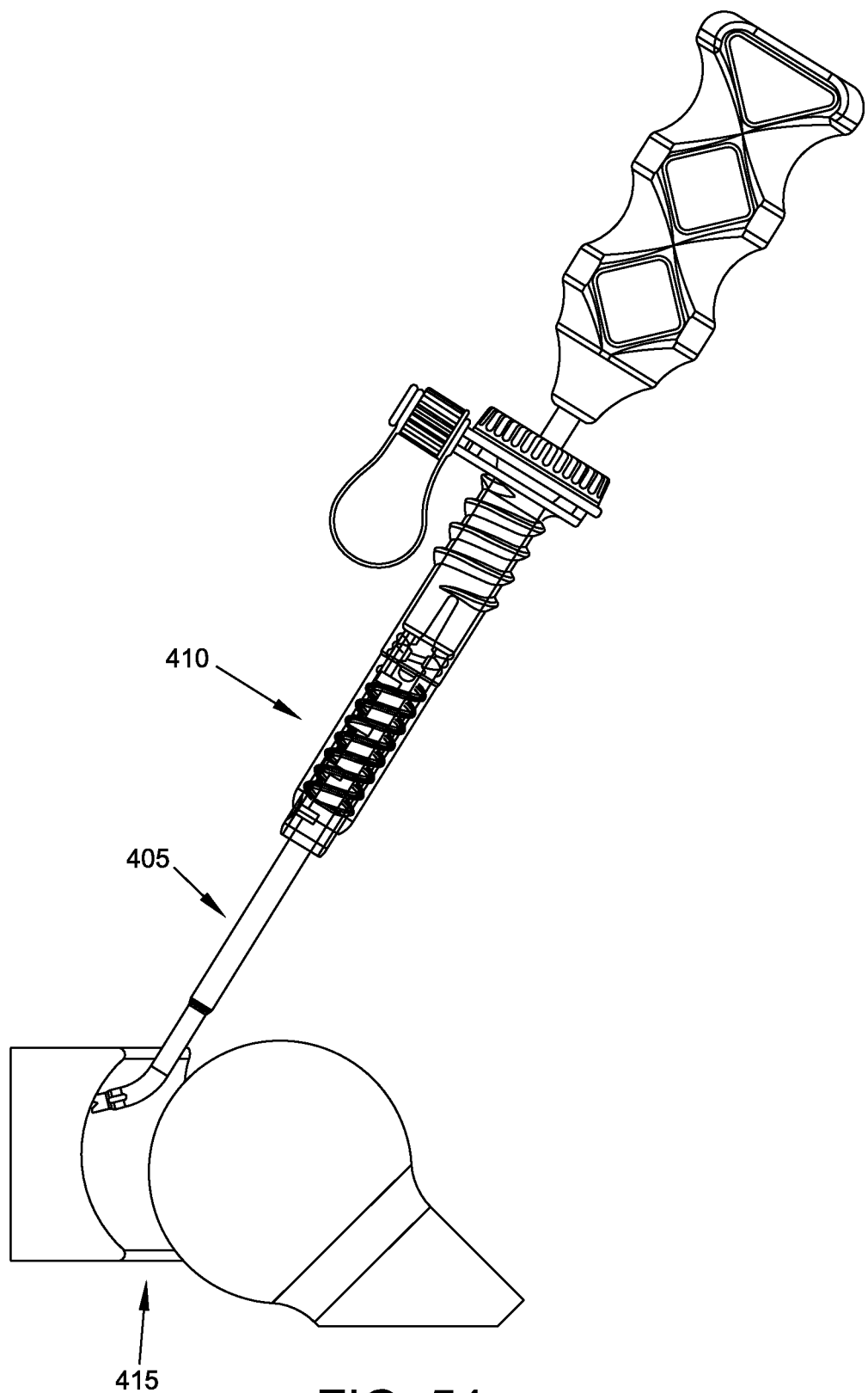
Figure 55:
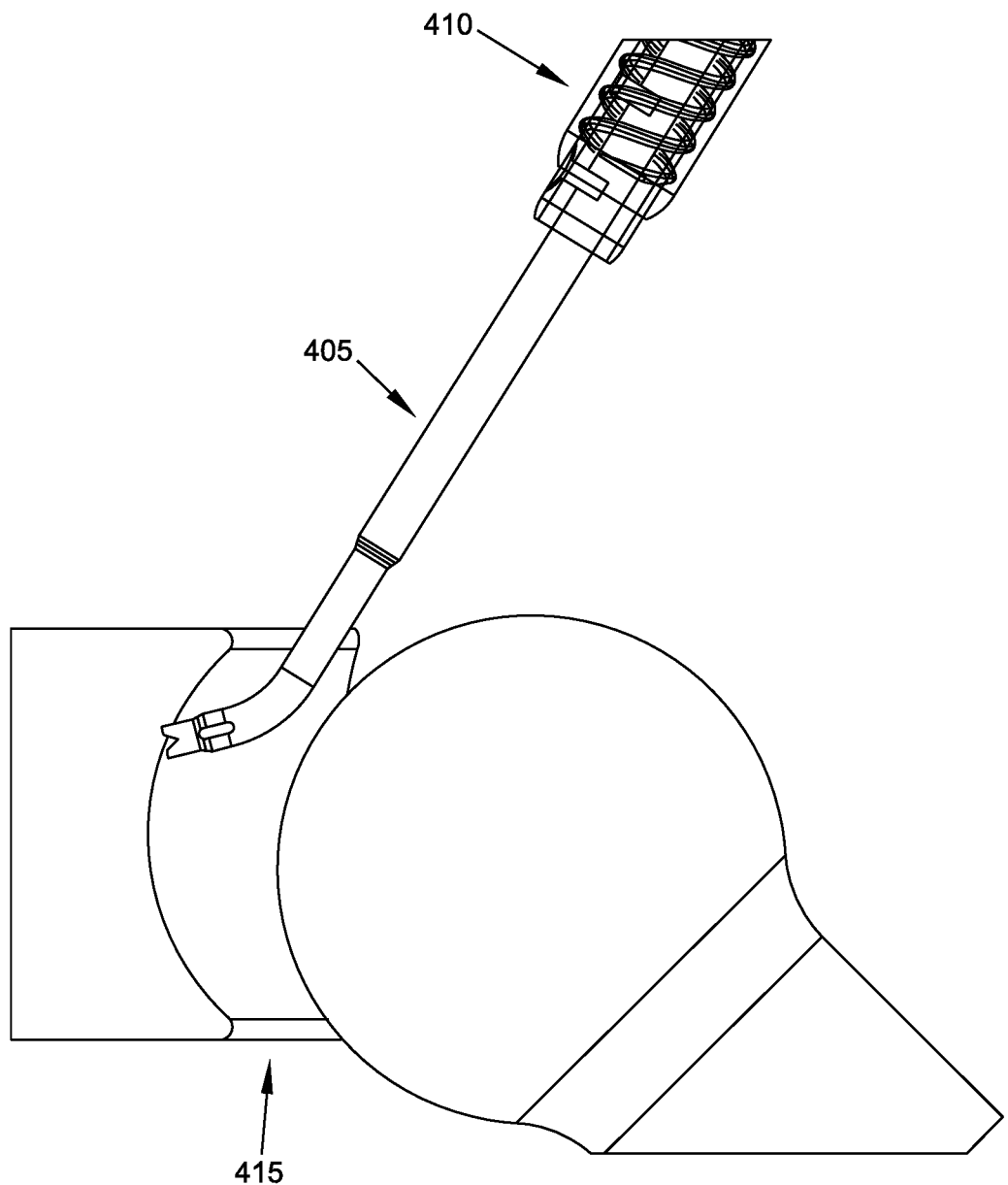
Figure 56:
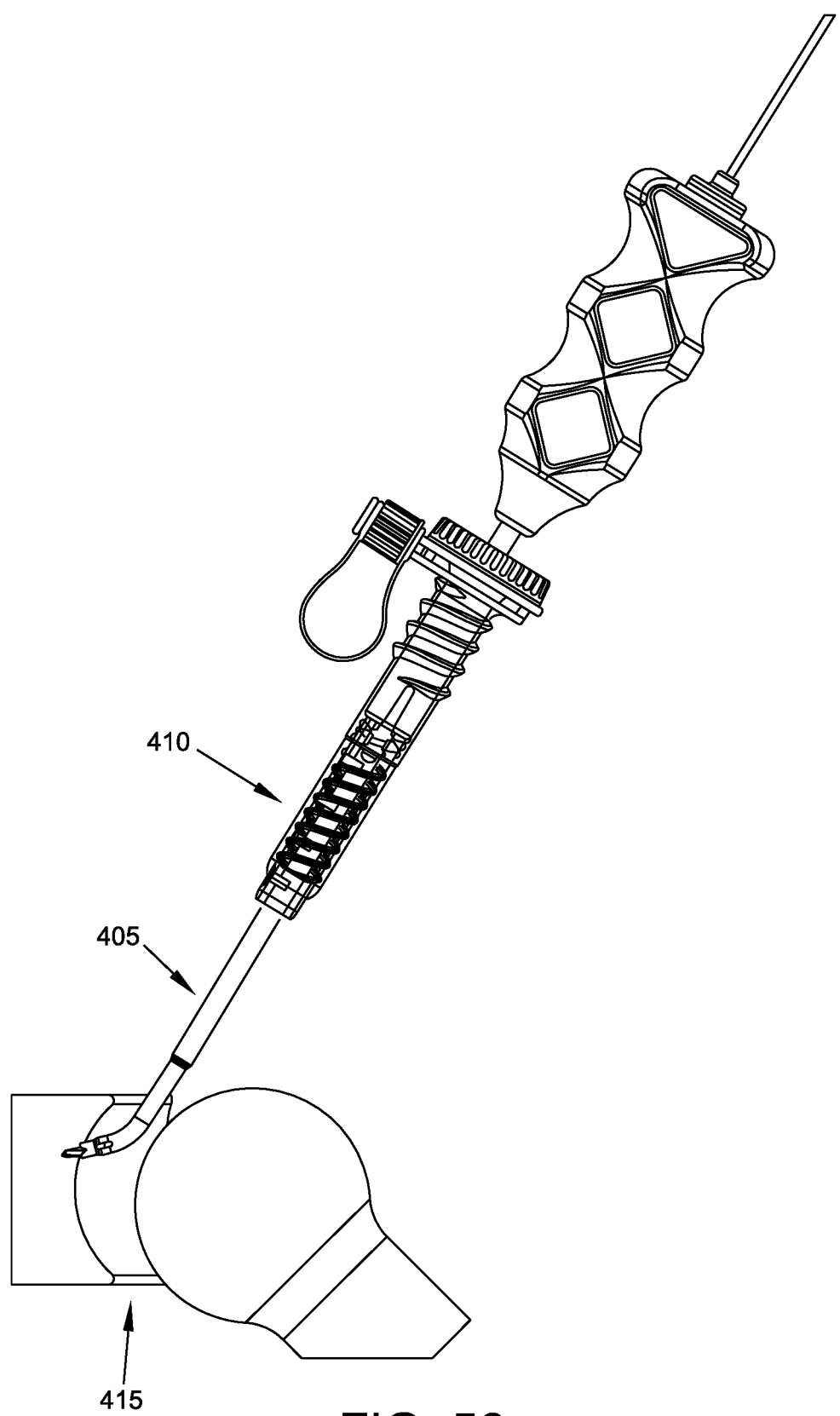
Figure 57:
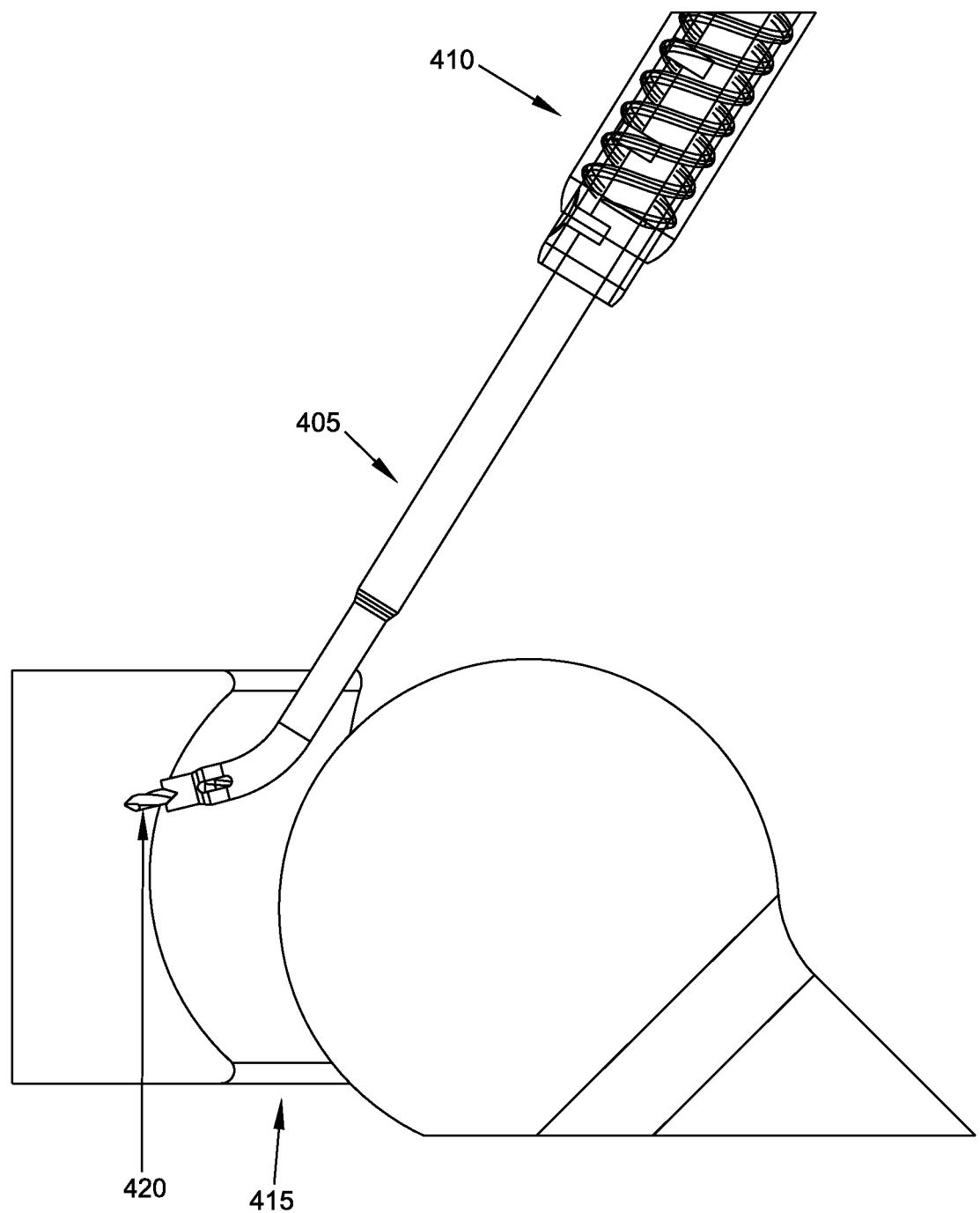

The provision of an articulating angled drill guide and flexible drill bit can be highly advantageous in numerous clinical situations, e.g., when drilling within the interior of a joint. Thus, for example, and looking now at FIGS. 50-57, there is shown an articulating angled drill guide 405 extending through an access cannula 410, with the distal end of articulating angled drill guide being disposed within the interior of a joint 415. More particularly, in this form of the invention, articulating angled drill guide 405 may be advanced into the interior of the joint with the articulating angled drill guide in a substantially straight configuration (FIGS. 50 and 51). This straight configuration may be helpful in providing a smaller profile by which to pass through the access cannula 410; it may also be helpful in entering a "tight" joint such as the hip joint where the space between the acetabular cup and femoral head is limited. Thereafter, the distal tip of articulating angled drill guide 405 is articulated into a curve so as to address a surface of the joint (FIGS. 52 and 53). Next, the distal end of articulating angled drill guide 405 is advanced so that the distal end of the articulating angled drill guide engages the surface which is to be drilled (FIGS. 54 and 55). Finally, a flexible drill bit 420 may be advanced through articulating angled drill guide 405 and drilled into the surface of the bone (FIGS. 56 and 57).

Friction-Reducing Flexible Drill Bit

In some situations the curvature of the flexible drill bit within an angled drill guide may be substantial, so that significant friction occurs between the flexible drill bit and the angled drill guide. When operated, the friction between the outer surface of the rotating flexible drill bit and the inner surface of the angled drill guide creates heat which will transfer to the flexible drill bit; a flexible drill bit operating at a higher temperature can have a reduced life. By way of example but not limitation, this can be important where a Nitinol flexible drill bit is operating in a highly stressed condition, so that the life of the Nitinol flexible drill bit is limited and is at or below the intended life of the drill bit to perform its function.

Figure 58:
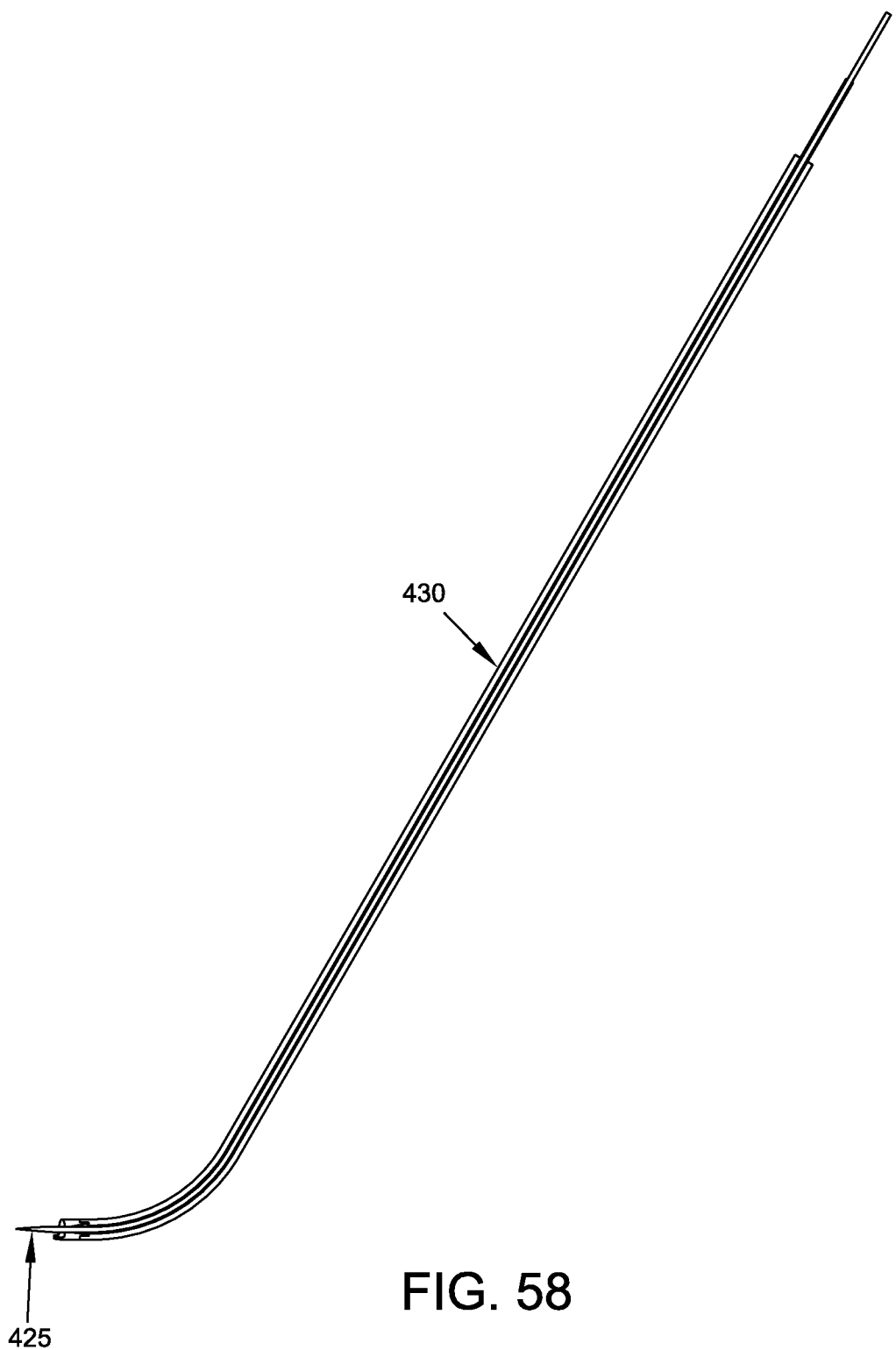
FIGS. 58-60 are schematic views showing a novel friction-reducing flexible drill bit formed in accordance with the present invention.
Figures 59, 60:
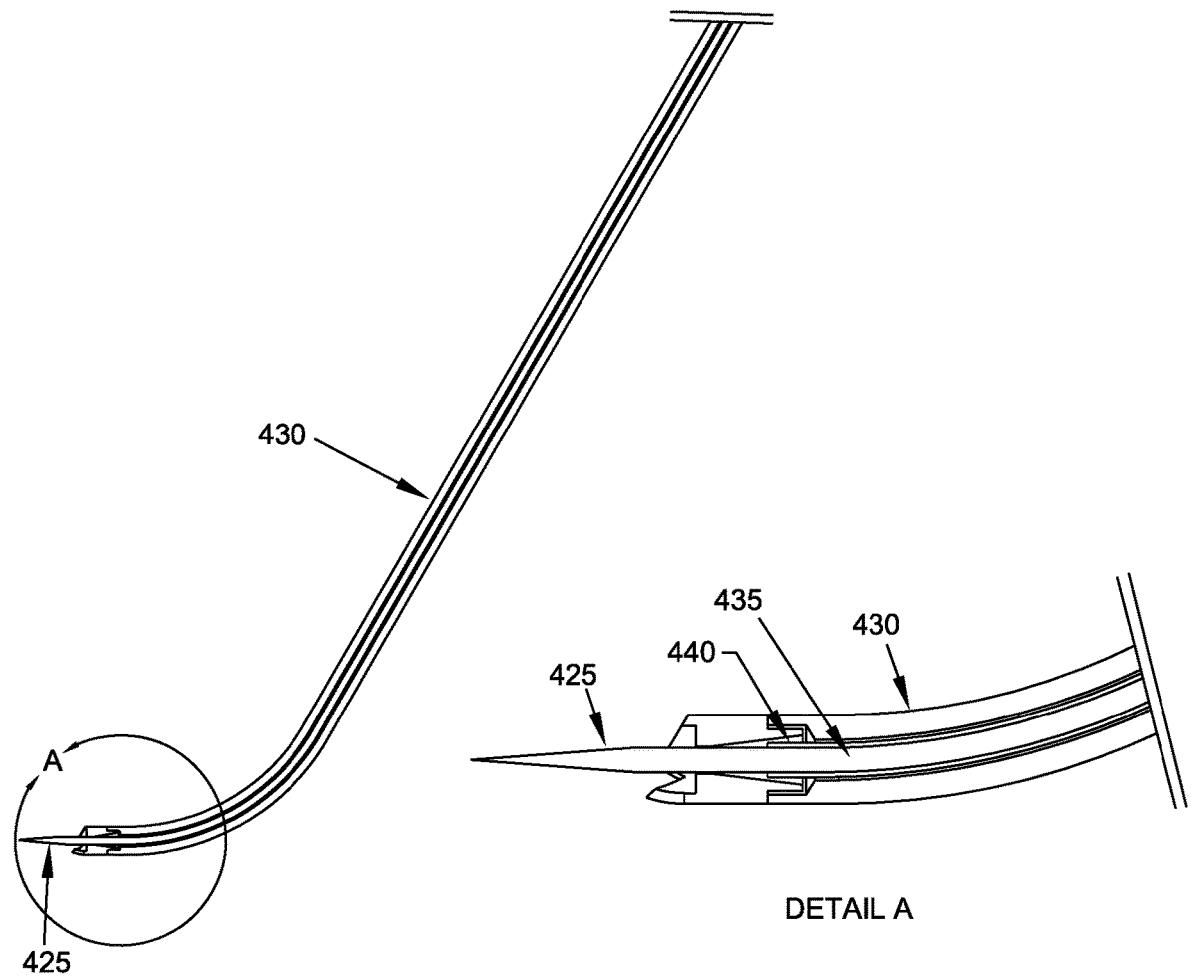

To this end, and looking now at FIGS. 58-60, a novel flexible drill bit 425 may be provided for use with an angled drill guide 430. Flexible drill bit 425 comprises a Nitinol (or other superelastic material) drill bit 435 having a low friction coating 440 on its outer surface. In one preferred form of the invention, low friction coating 440 comprises a polymer (e.g., PTFE) which is heat shrunk onto the outer diameter of Nitinol drill bit 435. By way of example, an angled drill guide was constructed with a distal end having a curve of approximately 60 degrees through an arc of approximately 1 inch radius. A Nitinol drill bit with a diameter of 0.0345 inch was constructed. The Nitinol drill bit was placed into the angled drill guide and operated. After approximately 4 minutes, the drill bit fractured. A second Nitinol drill bit was constructed with a diameter of 0.0345 inch, and a PTFE tube of approximately 0.008 inch thickness was heat shrunk onto the outer diameter of the Nitinol drill bit. The Nitinol drill bit with PTFE coating was placed into the angled drill guide and operated until it fractured, which occurred after approximately 8 minutes. It was found that the Nitinol drill bit with PTFE coating had a significantly longer life than the un-coated Nitinol drill bit in identical test conditions. This was attributed to the fact that the PTFE coating reduced friction between the inner diameter of the angled drill guide and outer diameter of the Nitinol drill bit; this enabled the construction to operate "cooler", which significantly extended the life of a Nitinol drill bit operating in a stressed condition.

MODIFICATIONS

While the present invention has been described in terms of certain exemplary preferred embodiments, it will be readily understood and appreciated by those skilled in the art that it is not so limited, and that many additions, deletions and modifications may be made to the preferred embodiments discussed herein without departing from the scope of the invention.

What is claimed is:

1. Apparatus for drilling into bone, the apparatus comprising:
   a distal cutting tip portion for drilling into bone; and
   a proximal shaft portion extending proximally from the distal cutting tip portion, wherein the proximal portion comprises a flexible portion having (i) sufficient longitudinal flexibility so as to permit the flexible portion of the proximal shaft portion to be passed along a curve, and (ii) sufficient torsional strength to permit the distal cutting tip portion to be turned into bone;

wherein the flexible portion is created by removing material from an outer diameter of the proximal shaft portion, wherein the material is removed in a spiral pattern to a depth less than a radius of the proximal shaft portion to leave a continuous length of material extending through the entire proximal shaft portion.

2. The apparatus as claimed in claim 1, wherein the proximal shaft portion and the distal cutting tip are formed from a single piece of material.

3. The apparatus as claimed in claim 1, wherein the spiral pattern defines an angle relative to a longitudinal axis of the proximal shaft portion.

4. The apparatus as claimed in claim 1, wherein the spiral pattern proceeds in a clockwise manner as it extends in a distal direction.

5. Apparatus according to claim 1 wherein the continuous length of material extends along a central axis of the proximal shaft portion.

6. Apparatus according to claim 1 wherein the material removed in the spiral pattern defines a continuous cut having a width, and wherein the width of the continuous cut is less than a longitudinal distance between adjacent turns of the continuous cut.

7. Apparatus according to claim 1 wherein the material removed in the spiral pattern defines a continuous cut with material remaining between adjacent turns of the continuous cut, and wherein the outer diameter of the material remaining between the adjacent turns of the continuous cut extends parallel to a central axis of the proximal shaft portion.

8. Apparatus according to claim 1 wherein the material removed in the spiral pattern defines a plurality of cuts, and wherein each of the cuts of the plurality of cuts is substantially perpendicular to a longitudinal axis of the proximal shaft portion.

9. Apparatus according to claim 1 wherein the material removed in the spiral pattern defines a plurality of cuts, and wherein each of the cuts of the plurality of cuts resides at least one of distal to an adjacent cut or proximal to an adjacent cut.

10. Apparatus for drilling into bone, the apparatus comprising:
a distal cutting tip portion; and
a proximal shaft portion comprising a first portion extending proximally from the distal cutting tip portion, a second portion extending proximally from the first portion and a solid inner region extending through the entire length of the first portion and the second portion;
wherein the first portion comprises a flexible portion having (i) sufficient longitudinal flexibility so as to permit the flexible portion of the proximal shaft portion to be passed along a curve, and (ii) sufficient torsional strength to permit the distal cutting tip portion to be turned into bone;
wherein the flexible portion is created by removing material radially inwardly from an outer diameter of the first portion of the proximal shaft portion to the solid inner region.

11. Apparatus according to claim 10 wherein the solid inner region extends along a central axis of the proximal shaft portion.

12. Apparatus according to claim 10 wherein the material removed defines a continuous cut having a width, and wherein the width of the continuous cut is less than a longitudinal distance between adjacent turns of the continuous cut.

13. Apparatus according to claim 10 wherein the material removed defines a continuous cut with material remaining between adjacent turns of the continuous cut, and wherein the outer diameter of the material remaining between the adjacent turns of the continuous cut extends parallel to a central axis of the proximal shaft portion.

14. Apparatus according to claim 10 wherein the material removed defines a plurality of cuts, and wherein each of the cuts of the plurality of cuts is substantially perpendicular to a longitudinal axis of a proximal shaft portion.

15. Apparatus according to claim 10 wherein the material removed defines a plurality of cuts, and wherein each of the cuts of the plurality of cuts resides at least one of distal to an adjacent cut or proximal to an adjacent cut.

16. The apparatus as claimed in claim 10 wherein the proximal shaft portion and the distal cutting tip are formed from a single piece of material.

17. The apparatus as claimed in claim 10 wherein the first portion and the second portion are formed integral with one another, and further wherein the distal cutting tip portion and the solid inner region are formed integral with one another.

18. The apparatus as claimed in claim 10 wherein the material removed defines an angle relative to a longitudinal axis of the proximal shaft portion.

19. Apparatus for drilling into bone, the apparatus comprising:
a distal cutting tip portion; and
a proximal shaft portion comprising a first portion extending proximally from the distal cutting tip portion, the first portion having a first outer surface, and a second portion extending proximally from the first portion, the second portion having a second outer surface;
wherein the first portion is formed by removing material inwardly in a continuous spiral pattern from the first outer surface of the first portion to a depth less than the radius of the first portion so as to provide a solid inner core extending the entire length of the first portion; and
wherein the distal cutting tip portion, the first portion and the second portion are all formed out of a single piece of material.

20. Apparatus according to claim 19 wherein the first outer surface and the second outer surface are aligned with one another.

21. Apparatus according to claim 19 wherein the solid inner core extends along a central axis of the proximal shaft portion.

22. Apparatus according to claim 19 wherein the material removed in the continuous spiral pattern defines a continuous cut having a width, and wherein the width of the continuous cut is less than a longitudinal distance between adjacent turns of the continuous cut.

23. Apparatus according to claim 19 wherein the material removed in the continuous spiral pattern defines a continuous cut with material remaining between adjacent turns of the continuous cut, and wherein the outer diameter of the material remaining between the adjacent turns of the continuous cut extends parallel to a central axis of the proximal shaft portion.

24. Apparatus according to claim 19 wherein the material removed in the continuous spiral pattern defines a plurality of cuts, and wherein each of the cuts of the plurality of cuts is substantially perpendicular to a longitudinal axis of the proximal shaft portion.

25. Apparatus according to claim 19 wherein the material removed in the continuous spiral pattern defines a plurality of cuts, and wherein each of the cuts of the plurality of cuts resides at least one of distal to an adjacent cut or proximal to an adjacent cut.

26. The apparatus as claimed in claim 19 wherein the continuous spiral pattern defines an angle relative to a longitudinal axis of the proximal shaft portion.

27. The apparatus as claimed in claim 19 wherein the continuous spiral pattern proceeds in a clockwise manner as it extends in a distal direction.

\* \* \* \* \*